United States Patent
Hu et al.

(10) Patent No.: US 9,242,991 B2
(45) Date of Patent: Jan. 26, 2016

(54) SUBSTITUTED FUSED HETEROCYCLES AS C-MET TYROSINE KINASE INHIBITORS

(75) Inventors: Shaojing Hu, Beijing (CN); Fei Wang, Beijing (CN); Wei Long, Beijing (CN); Xiaoyan Shen, Beijing (CN); Fenlai Tan, Beijing (CN); Yinxiang Wang, Beijing (CN)

(73) Assignee: BETTA PHARMACEUTICALS CO., LTD, Hangzhou (CN)

( * ) Notice: Subject to any disclaimer, the term of this patent is extended or adjusted under 35 U.S.C. 154(b) by 0 days.

(21) Appl. No.: 13/809,836

(22) PCT Filed: Jul. 14, 2011

(86) PCT No.: PCT/CN2011/077169
§ 371 (c)(1),
(2), (4) Date: Jan. 11, 2013

(87) PCT Pub. No.: WO2012/006960
PCT Pub. Date: Jan. 19, 2012

(65) Prior Publication Data
US 2013/0123286 A1    May 16, 2013

(30) Foreign Application Priority Data
Jul. 14, 2010  (WO) ................ PCT/CN2010/001060

(51) Int. Cl.
| | | |
|---|---|---|
| A61K 31/519 | (2006.01) | |
| A61K 31/4353 | (2006.01) | |
| C07D 491/14 | (2006.01) | |
| C07D 491/04 | (2006.01) | |
| C07D 498/04 | (2006.01) | |

(52) U.S. Cl.
CPC ............ *C07D 491/04* (2013.01); *C07D 498/04* (2013.01)

(58) Field of Classification Search
CPC . A61K 31/519; A61K 31/4353; C07D 491/14
USPC ............ 514/267, 291; 544/250, 333; 546/90, 546/268.1; 548/311.7, 373.1
See application file for complete search history.

(56) References Cited

U.S. PATENT DOCUMENTS 8,673,917 B2 *   3/2014   Zoller et al. ............. 514/252.06

FOREIGN PATENT DOCUMENTS

WO    WO 2012/006960    *   1/2012

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*
Wolff, Manfred E., Ed. Burger's Medicinal Chemistry and Drug Discovery—Fifth Edition, New York: John Wiley & Sons, 1996, 1, 975-976.*

* cited by examiner

*Primary Examiner* — Douglas M Willis
(74) *Attorney, Agent, or Firm* — Weisun Rao; Greenberg Traurig, LLP

(57) ABSTRACT

This invention relates to certain novel fused quinazoline derivatives (Formula I) as c-Met inhibitors which is shown as formula I, their synthesis and their use for treating a c-Met mediated disorder. More particularly, this invention is directed to fused heterocyclic derivatives useful inhibitors of c-Met, methods for producing such compounds and methods for treating as c-Met mediated disorder

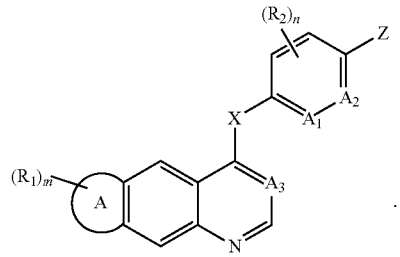

Formula 1

43 Claims, No Drawings

SUBSTITUTED FUSED HETEROCYCLES AS C-MET TYROSINE KINASE INHIBITORS

CROSS-REFERENCE TO RELATED APPLICATIONS

This application is a national phase application based on PCT/CN2011/077169, filed on Jul. 14, 2011, which claims priority of PCT/CN2010/001060, filed on Jul. 14, 2010, both of which are incorporated herein by reference.

FIELD OF THE INVENTION

This invention relates to certain novel fused quinazoline derivatives as c-Met inhibitors, their synthesis and their use for treating a c-Met mediated disorder. More particularly, this invention is directed to fused heterocyclic derivatives useful as inhibitors of c-Met, methods for producing such compounds and methods for treating a c-Met-mediated disorder.

BACKGROUND OF THE INVENTION

The study of signal transduction pathways in normal and pathological states is of considerable interest because of the potential therapeutic benefit arising from new molecular agents targeting certain of these pathways associated with disease.

Receptor tyrosine kinases (RTKs) are key enzymes in signal transduction pathways that catalyze the autophosphorylation of tyrosine residues within the cytosolic, C-terminal domain of the protein. This generates docking sites for the recruitment of downstream proteins and the subsequent propagation of signals involved in an array of cellular events including growth, proliferation and survival. More generally deregulated kinase signaling is implicated in a diverse range of pathological states including immunological and inflammatory disorders, cardiovascular and neurodegenerative disease. The known receptor tyrosine kinases encompass 20 families and many are oncogenes (Blume-Jensen P et al. 2001. Nature 411 355-365). c-Met is the prototypic member of a subfamily of RTKs which includes the related proteins Ron (macrophage-stimulating protein receptor) and its chicken orthologue, Sea. The endogenous ligand is the growth and motility factor hepatocyte growth factor (HGF, also known as Scatter Factor). c-Met and HGF are expressed in a range of tissue types although their expression is normally restricted to cells of epithelial and mesenchymal origin. In contrast, tumor cells often express constitutively activated c-Met.

There is now a growing body of compelling evidence from both animal studies and cancer patients that HGF-Met signaling plays an important role in the development and progression of malignancy and is associated in particular with invasive phenotypes. c-Met and HGF are highly expressed relative to surrounding tissue in numerous cancers and their expression correlates with poor patient prognosis (Jiang, W et al. 1999 Crit. Rev. Oncol. Hematol., 29, 209-248.) Activating point mutations in the kinase domain of c-Met are implicated in the cause of sporadic and hereditary forms of papillary renal carcinoma (Danilkovitch-Miagkova, A et al 2002. 1 J. Clin. Invest. 109, 863-867). c-Met is a marker for both cancer and malignancy and agents that inhibit c-Met-HGF signaling can be expected to ameliorate disease progression in relevant cancers.

SUMMARY OF THE INVENTION

It has now been found that a novel class of fused pyridines are effective inhibitors of c-Met. The present invention is directed to novel compounds having c-Met inhibitory activity. The compounds of the invention have the general structure as Formula I:

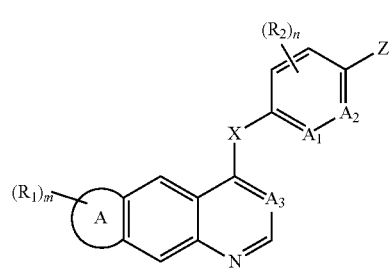

formula I wherein
A is a 5-18 membered ring;
$R_1$ is selected from the group consisting of hydrogen, halogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alkynyloxy, $C_{1-8}$alkylthio, N—($C_{1-8}$alkyl) carbamoyl, N, N-di($C_{1-8}$alkyl) carbamoyl, $C_{1-8}$alkanoyloxy, $C_{1-8}$alkanoylamino, $C_{3-8}$alkynoylamino, N—($C_{1-8}$alkyl) sulfamoyl, and N, N-di($C_{1-8}$alkyl) sulfamoyl;
m is an integer from 0 to 3;
$A_1$ and $A_2$ are each independently selected from =N—, =C($R_2$)—;
$A_3$ is selected from =N—, =C(H)—, and =C(CN)—;
X is selected from the group consisting of $NR_{20}$, $CHR_{21}$, O, or S; the said $R_{20}$ and $R_{21}$ are each independently H or $C_{1-8}$alkyl;
$R_2$ is selected from —H, halogen, trihalomethyl, —CN, —NO$_2$, —NH$_2$, —OR$_5$, —NR$_5$R$_6$, —S(O)$_{0-2}$R$_5$, —SO$_2$NR$_5$R$_6$, —CO$_2$R$_5$, —C(O)NR$_5$R$_6$, —N(R$_3$)SO$_2$R$_5$, —N(R$_5$)C(O)R$_6$, —N(R$_5$)CO$_2$R$_6$, —C(O)R$_5$, and optionally substituted lower alkyl;
n is 0 to 4;
Z is selected from NR$_3$R$_4$ or group having Formula II

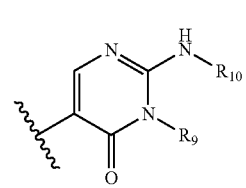

Formula II $R_3$ is independent selected from the group consisting of hydrogen, substituted or unsubstituted $C_{1-8}$alkyl, substituted or unsubstituted $C_{2-8}$alkenyl, substituted or unsubstituted $C_{2-8}$alkynyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alkynyloxy, $C_{1-8}$alkylthio, N—($C_{1-8}$ alkyl) carbamoyl, N,N-di($C_{1-8}$alkyl) carbamoyl, $C_{1-8}$alkanoyloxy, $C_{1-8}$alkanoylamino, $C_{3-8}$alkynoylamino, N—($C_{1-8}$alkyl) sulfamoyl, and N,N-di($C_{1-8}$alkyl) sulfamoyl;

In one preferred embodiment, R$_4$ is selected from the group having Formula III:

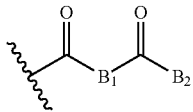

Formula III

B$_1$ is

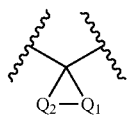

Q$_1$ is C(R$_5$)$_2$;

B$_2$ is NHQ$_2$;

Q$_2$ is selected from the group consisting of substituted or unsubstituted aryl, substituted or unsubstituted heteroaryl, substituted or unsubstituted heterocyclyl, substituted or unsubstituted C$_{1-8}$alkylaryl, substituted or unsubstituted C$_{1-8}$alkylheteroaryl, substituted or unsubstituted C$_{1-8}$alkylheterocyclyl;

B$_1$ and B$_2$ together may form 5 to 10 member substituted or unsubstituted heteroaryl, substituted or unsubstituted heterocyclyl;

R$_5$ and R$_6$ are each independently selected from the group consisting of hydrogen, halogen, substituted or unsubstituted C$_{1-8}$alkyl, substituted or unsubstituted C$_{2-8}$alkenyl, substituted or unsubstituted C$_{2-8}$alkynyl, substituted or unsubstituted aryl, substituted or unsubstituted heteroaryl, substituted or unsubstituted heterocyclyl, C$_{1-8}$alkanoyl, C$_{1-8}$alkoxycarbonyl, C$_{1-8}$alkylsulfinyl, C$_{1-8}$alkylsulfonyl, arylsulfonyl, cyano, nitro, hydroxy, amino, carboxy, oxo, carbamoyl, C$_{1-8}$alkoxy, C$_{2-8}$alkenyloxy, C$_{2-8}$alknyloxy, C$_{1-8}$alkylthio, N—(C$_{1-8}$alkyl) carbamoyl, N, N-di(C$_{1-8}$alkyl) carbamoyl, C$_{1-8}$alkanoyloxy, C$_{1-8}$alkanoylamino, C$_{3-8}$alkynoylamino, N—(C$_{1-8}$alkyl) sulfamoyl, and N, N-di(C$_{1-8}$alkyl) sulfamoyl; substituted or unsubstituted C$_{1-8}$alkylaryl, substituted or unsubstituted C$_{1-8}$alkylheteroaryl, substituted or unsubstituted C$_{1-8}$alkylheterocyclyl; and pharmaceutically acceptable salts thereof;

In one preferred embodiment, ring A further comprises that 0 to 6 heteroatoms selected from the group consisting of O, S, and N.

In a preferred embodiment, R$_1$ is selected from the group consisting hydrogen, halogen, C$_{1-8}$alkyl, C$_{2-8}$alkenyl, C$_{2-8}$alkynyl, aryl, heteroaryl, heterocyclyl, (halo)$_{1-3}$(C$_{1-8}$)alkyl, hydroxy (C$_{1-8}$)alkyl, C$_{1-4}$alkoxy(C$_{1-8}$) alkyl, cyano (C$_{1-8}$) alkyl, amino (C$_{1-8}$)alkyl, aryl (C$_{1-8}$) alkyl, heteroaryl (C$_{1-8}$) alkyl, heterocyclyl (C$_{1-8}$) alkyl, (halo)$_{1-3}$(C$_{2-8}$) alkenyl, hydroxy(C$_{2-8}$)alkenyl, (C$_{1-4}$alkoxy(C$_{2-8}$)alkenyl, cyano (C$_{2-8}$)alkenyl, and amino(C$_{2-8}$)alkenyl, aryl(C$_{2-8}$)alkenyl, heteroaryl(C$_{2-8}$)alkenyl, heterocyclyl(C$_{2-8}$)alkenyl, (halo)$_{1-3}$(C$_{2-8}$)alkynyl, hydroxy(C$_{2-8}$)alkynyl, C$_{1-4}$alkoxy(C$_{2-8}$)alkynyl, cyano(C$_{2-8}$)alkynyl, amino(C$_{2-8}$)alkynyl, aryl(C$_{2-8}$)alkynyl, heteroaryl (C$_{2-8}$)alkynyl, heterocyclyl(C$_{2-8}$)alkynyl, C$_{1-8}$alkanoyl, aryl (C$_{1-8}$) alkanoyl, heteroaryl(C$_{1-8}$) alkanoyl, heterocyclyl(C$_{1-8}$)alkanoyl, C$_{1-8}$alkoxycarbonyl, aryl(C$_{1-8}$) alkoxycarbonyl, heteroaryl (C$_{1-8}$)alkoxycarbonyl, heterocyclyl(C$_{1-8}$)alkoxycarbonyl, C$_{1-8}$alkylsulfinyl, C$_{1-8}$alkylsulfonyl, arylsulfonyl, aryl(C$_{1-8}$)alkylsulfonyl, heteroaryl (C$_{1-8}$) alkylsulfonyl, heterocyclyl(C$_{1-8}$) alkylsulfonyl, aryl, heteroaryl, heterocyclyl, cyano, nitro, hydroxy, amino, carboxy, oxo, carbamoyl, C$_{1-8}$alkoxy, C$_{2-8}$alkenyloxy, C$_{2-8}$alknyloxy, C$_{1-8}$alkylthio, N—(C$_{1-8}$alkyl) carbamoyl, N, carbamoyl, C$_{1-8}$alkanoyloxy, C$_{1-8}$alkanoylamino, C$_{3-8}$alknoylamino, N—(C$_{1-8}$alkyl) sulfamoyl, and N, N-di-(C$_{1-8}$alkyl) sulfamoyl.

In another preferred embodiment, the above amino, amino (C$_{1-8}$) alkyl, amino (C$_{2-8}$) alkenyl or amino (C$_{2-8}$) alkynyl within R$_1$ is substituted with two substituents independently selected from the group consisting of hydrogen, C$_{1-8}$alkyl, C$_{2-8}$alkenyl, C$_{2-8}$alkynyl.

In another preferred embodiment, any aryl, heteroaryl or heterocyclyl group within optionally bears one to three substituents independently selected from halogeno, trifluoromethyl, cyano, nitro, hydroxy, amino, carboxy, carbamoyl, (C$_{1-8}$) alkyl, (C$_{2-8}$) alkenyl, (C$_{2-8}$)alkynyl, (C$_{1-8}$)alkoxy.

In another preferred embodiment, R$_3$ is independent selected from the group consisting of hydrogen, substituted or unsubstituted C$_{1-8}$alkyl, substituted or unsubstituted C$_{2-8}$alkenyl, substituted or unsubstituted C$_{2-8}$alkynyl, C$_{1-8}$alkanoyl, C$_{1-8}$alkoxycarbonyl, C$_{1-8}$alkylsulfonyl, arylsulfonyl, cyano, nitro, hydroxy, amino, carboxy, oxo, carbamoyl, C$_{1-8}$alkoxy, C$_{2-8}$alkenyloxy, C$_{2-8}$alknyloxy, C$_{1-8}$alkylthio, N—(C$_{1-8}$alkyl) carbamoyl, N,N-di(C$_{1-8}$alkyl) carbamoyl, C$_{1-8}$alkanoyloxy, C$_{1-8}$alkanoylamino, C$_{3-8}$alkynoylamino, N—(C$_{1-8}$alkyl) sulfamoyl, and N, N-di(C$_{1-8}$alkyl) sulfamoyl;

In another preferred embodiment, R$_4$ is selected from the group having Formula IV:

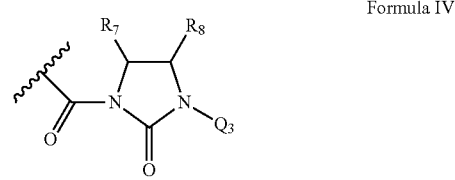

Formula IV wherein

Q$_3$ is selected from the group consisting of substituted or unsubstituted aryl, substituted or unsubstituted heteroaryl, substituted or unsubstituted heterocyclyl, substituted or unsubstituted C$_{1-8}$alkylaryl, substituted or unsubstituted C$_{1-8}$alkylheteroaryl, substituted or unsubstituted C$_{1-8}$alkylheterocyclyl;

R$_7$ and R$_8$ are each independently selected from the group consisting of hydrogen, halogen, substituted or unsubstituted C$_{1-8}$alkyl, substituted or unsubstituted C$_{2-8}$alkenyl, substituted or unsubstituted C$_{2-8}$alkynyl, substituted or unsubstituted aryl, substituted or unsubstituted heteroaryl, substituted or unsubstituted heterocyclyl, C$_{1-8}$alkanoyl, C$_{1-8}$alkoxycarbonyl, C$_{1-8}$alkylsulfinyl, C$_{1-8}$alkylsulfonyl, arylsulfonyl, cyano, nitro, hydroxy, amino, carboxy, oxo, carbamoyl, C$_{1-8}$alkoxy, C$_{2-8}$alkenyloxy, C$_{2-8}$alknyloxy, C$_{1-8}$alkylthio, N—(C$_{1-8}$alkyl) carbamoyl, N, N-di(C$_{1-8}$alkyl) carbamoyl, C$_{1-8}$alkanoyloxy, C$_{1-8}$alkanoylamino, C$_{3-8}$alkynoylamino, N—(C$_{1-8}$alkyl) sulfamoyl, and N, N-di(C$_{1-8}$alkyl) sulfamoyl; substituted or unsubstituted C$_{1-8}$alkylaryl, substituted or unsubstituted C$_{1-8}$alkylheteroaryl, substituted or unsubstituted C$_{1-8}$alkylheterocyclyl;

In another preferred embodiment, R$_3$ is independent selected from the group consisting of hydrogen, substituted or unsubstituted C$_{1-8}$alkyl, substituted or unsubstituted C$_{2-8}$alkenyl, substituted or unsubstituted C$_{2-8}$alkynyl, C$_{1-8}$alkanoyl, C$_{1-8}$alkoxycarbonyl, C$_{1-8}$alkylsulfinyl, C$_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alknyloxy, $C_{1-8}$alkylthio, N—($C_{1-8}$alkyl) carbamoyl, N, N-di($C_{1-8}$alkyl) carbamoyl, $C_{1-8}$alkanoyloxy, $C_{1-8}$alkanoylamino, $C_{3-8}$alkynoylamino, N—($C_{1-8}$alkyl) sulfamoyl, and N, N-di($C_{1-8}$alkyl) sulfamoyl;

In another preferred embodiment, $R_4$ is selected from the group having Formula V:

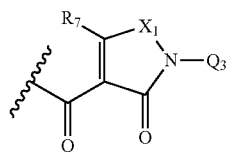

Formula V wherein $Q_3$ is selected from the group consisting of substituted or unsubstituted aryl, substituted or unsubstituted heteroaryl, substituted or unsubstituted heterocyclyl, substituted or unsubstituted $C_{1-8}$alkylaryl, substituted or unsubstituted $C_{1-8}$alkylheteroaryl, substituted or unsubstituted $C_{1-8}$alkylheterocyclyl;

$X_1$ is selected from the group consisting of $NR_8$, $CR_7R_5$;

$R_7$ and $R_8$ are each independently selected from the group consisting of hydrogen, halogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alknyloxy, $C_{1-8}$alkylthio, N—($C_{1-8}$alkyl) carbamoyl, N, N-di($C_{1-8}$alkyl) carbamoyl, $C_{1-8}$alkanoyloxy, $C_{1-8}$alkanoylamino, $C_{3-8}$alkynoylamino, N—($C_{1-8}$alkyl) sulfamoyl, and N, N-di($C_{1-8}$alkyl) sulfamoyl; substituted or unsubstituted $C_{1-8}$alkylaryl, substituted or unsubstituted $C_{1-8}$alkylheteroaryl, substituted or unsubstituted $C_{1-8}$alkylheterocyclyl;

In another preferred embodiment, $R_3$ is independent selected from the group consisting of hydrogen, substituted or unsubstituted $C_{1-8}$alkyl, substituted or unsubstituted $C_{2-8}$alkenyl, substituted or unsubstituted $C_{2-8}$alkynyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alknyloxy, $C_{1-8}$alkylthio, N—($C_{1-8}$alkyl) carbamoyl, N, N-di($C_{1-8}$alkyl) carbamoyl, $C_{1-8}$alkanoyloxy, $C_{1-8}$alkanoylamino, $C_{3-8}$alkynoylamino, N—($C_{1-8}$alkyl) sulfamoyl, and N, N-di($C_{1-8}$alkyl) sulfamoyl;

In another preferred embodiment, $R_4$ is selected from the group having Formula VI:

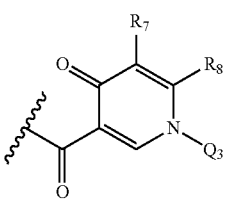

Formula VI wherein $Q_3$ is selected from the group consisting of substituted or unsubstituted aryl, substituted or unsubstituted heteroaryl, substituted or unsubstituted heterocyclyl, substituted or unsubstituted $C_{1-8}$alkylaryl, substituted or unsubstituted $C_{1-8}$alkylheteroaryl, substituted or unsubstituted $C_{1-8}$alkylheterocyclyl;

$R_7$ and $R_8$ are each independently selected from the group consisting of hydrogen, halogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alknyloxy, $C_{1-8}$alkylthio, N—($C_{1-8}$alkyl) carbamoyl, N, N-di($C_{1-8}$alkyl) carbamoyl, $C_{1-8}$alkanoyloxy, $C_{1-8}$alkanoylamino, $C_{3-8}$alkynoylamino, N—($C_{1-8}$alkyl) sulfamoyl, and N, sulfamoyl; substituted or unsubstituted $C_{1-8}$alkylaryl, substituted or unsubstituted $C_{1-8}$alkylheteroaryl, substituted or unsubstituted $C_{1-8}$alkylheterocyclyl;

In another preferred embodiment, $R_4$ is selected from the group having Formula VII:

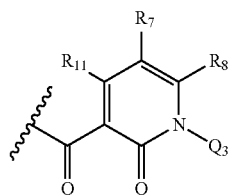

Formula VII wherein $Q_3$ is selected from the group consisting of substituted or unsubstituted aryl, substituted or unsubstituted heteroaryl, substituted or unsubstituted heterocyclyl, substituted or unsubstituted $C_{1-8}$alkylaryl, substituted or unsubstituted $C_{1-8}$alkylheteroaryl, substituted or unsubstituted $C_{1-8}$alkylheterocyclyl;

$R_7$, $R_8$ and $R_{11}$ are each independently selected from the group consisting of hydrogen, halogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alknyloxy, N—($C_{1-8}$alkyl)carbamoyl, N, N-di($C_{1-8}$alkyl)carbamoyl, $C_{1-8}$alkanoyloxy, $C_{1-8}$alkanoylamino, $C_{3-8}$alkynoylamino, N—($C_{1-8}$alkyl)sulfamoyl, and N, N-di($C_{1-8}$alkyl)sulfamoyl; substituted or unsubstituted $C_{1-8}$alkylaryl, substituted or unsubstituted $C_{1-8}$alkylheteroaryl, substituted or unsubstituted $C_{1-8}$alkylheterocyclyl;

$R_9$ and $R_{10}$ are each independently selected from the group consisting of substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, $C_{1-8}$alkoxycarbonyl, $C_{1-8}$alkylsulfinyl, $C_{1-8}$alkylsulfonyl, arylsulfonyl.

The flowing compounds of the invention are provided to give the reader an understanding of the compounds encompassed by the invention:

5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1,3-diaza-cyclododeca[b]naphthalen-4-yloxy)-phenyl]-amide;

1-(4-Fluoro-phenyl)-2-oxo-1,2-dihydro-pyridine-3-carboxylic acid [3-fluoro-4-(7,8,10,11,13,14-hexahydro-6,9,12,15-tetraoxa-1,3-diaza-cyclododeca[b]naphthalen-4-yloxy)-phenyl]-amide;

Cyclopropane-1,1-dicarboxylic acid[3-fluoro-4-(7,8,10,11,13,14-hexahydro-6,9,12,15-tetraoxa-1,3-diaza-yclododeca[b]naphthalen-4-yloxy)-phenyl]-amide(4-fluoro-phenyl)-amide;

3-(4-Fluoro-phenyl)-2-oxo-imidazolidine-1-carboxylic acid [3-fluoro-4-(7,8,10,11,13,14-hexahydro-6,9,12,15-tetraoxa-1,3-diaza-cyclododeca[b]naphthalen-4-yloxy)-phenyl]-amide;

2-(4-Fluoro-phenyl)-1,5-dimethyl-3-oxo-2,3-dihydro-1H-pyrazole-4-carboxylic acid [3-fluoro-4-(7,8,10,11,13,14-hexahydro-6,9,12,15-tetraoxa-1,3-diaza-cyclododeca[b]naphthalen-4-yloxy)-phenyl]-amide;

2-(4-Fluoro-phenylamino)-5-[5-(7,8,10,11,13,14-hexahydro-6,9,12,15-tetraoxa-1,3-diaza-cyclododeca[b]naphthalen-4-yloxy)-pyridin-2-yl]-3-methyl-3H-pyrimidin-4-one;

5-[5-([1,3]Dioxolo[4,5-g]quinazolin-8-yloxy)-pyridin-2-yl]-2-(4-fluoro-phenylamino)-3-methyl-3H-pyrimidin-4-one;

5-[5-(2,2-Difluoro-[1,3]dioxolo[4,5-g]quinazolin-8-yloxy)-pyridin-2-yl]-2-(4-fluoro-phenylamino)-3-methyl-3H-pyrimidin-4-one;

5-(4-Fluoro-phenyl)-4-oxo-1,4-dihydro-pyridine-3-carboxylic acid [4-([1,3]dioxolo[4,5-g]quinazolin-8-yloxy)-3-fluoro-phenyl]-amide;

5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1-aza-cyclododeca[b]naphthalen-4-yloxy)-phenyl]-amide;

1-(4-Fluoro-phenyl)-2-oxo-1,2-dihydro-pyridine-3-carboxylic acid [3-fluoro-4-(7,8,10,11,13,14-hexahydro-6,9,12,15-tetraoxa-1-aza-cyclododeca[b]naphthalen-4-yloxy)-phenyl]-amide;

2-(4-Fluoro-phenyl)-1,5-dimethyl-3-oxo-2,3-dihydro-1H-pyrazole-4-carboxylic acid [3-fluoro-4-(7,8,10,11,13,14-hexahydro-6,9,12,15-tetraoxa-1-aza-cyclododeca[b]naphthalen-4-yloxy)-phenyl]-amide;

Cyclopropane-1,1-dicarboxylic acid[3-fluoro-4-(7,8,10,11,13,14-hexahydro-6,9,12,15-tetraoxa-1-aza-cyclododeca[b]naphthalen-4-yloxy)-phenyl]-amide (4-fluoro-phenyl)-amide;

3-(4-Fluoro-phenyl)-2-oxo-imidazolidine-1-carboxylic acid [3-fluoro-4-(7,8,10,11,13,14-hexahydro-6,9,12,15-tetraoxa-1-aza-cyclododeca[b]naphthalen-4-yloxy)-phenyl]-amide;

5-[5-(2,2-Difluoro-[1,3]dioxolo[4,5-g]quinazolin-8-yloxy)-pyridin-2-yl]-2-(2-fluoro-phenylamino)-3-methyl-3H-pyrimidin-4-one;

5-[5-(2,2-Difluoro-[1,3]dioxolo[4,5-g]quinazolin-8-yloxy)-pyridin-2-yl]-2-(phenylamino)-3-methyl-3H-pyrimidin-4-one;

5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1-aza-cyclododeca[b]naphthalen-4-ylamino)-phenyl]-amide;

5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1-aza-cyclododeca[b]naphthalen-4-ylsulfanyl)-phenyl]-amide;

3-Methyl-2-phenylamino-5-[5-(2,5,7,10-tetraoxa-14,16-diaza-tricyclo[9.8.0.013,18]nonadeca-1(11),12,14,16,18-pentaen-17-yloxy)-pyridin-2-yl]-3H-pyrimidin-4-one;

5-[5-(8,9-Dihydro-7H-6,10-dioxa-1,3-diaza-cyclohepta[b]naphthalen-4-yloxy)-pyridin-2-yl]-2-(4-fluoro-phenylamino)-3-methyl-3H-pyrimidin-4-one;

2-(4-Fluoro-phenylamino)-3-methyl-5-[5-(9-methyl-8,9,10,11-tetrahydro-7H-6,12-dioxa-1,3,9-triaza-cyclonona[b]naphthalen-4-yloxy)-pyridin-2-yl]-3H-pyrimidin-4-one;

2-(4-Fluoro-phenylamino)-3-methyl-5-[5-(7,8,10,11-tetrahydro-6,9,12-trioxa-1,3-diaza-cyclonona[b]naphthalen-4-yloxy)-pyridin-2-yl]-3H-pyrimidin-4-one;

5-[5-(8,9-Dihydro-7H-6,10-dioxa-1-aza-cyclohepta[b]naphthalen-4-yloxy)-pyridin-2-yl]-2-(4-fluoro-phenylamino)-3-methyl-3H-pyrimidin-4-one;

2-(4-Fluoro-phenylamino)-3-methyl-5-[5-(9-methyl-8,9,10,11-tetrahydro-7H-6,12-dioxa-1,9-diaza-cyclonona[b]naphthalen-4-yloxy)-pyridin-2-yl]-3H-pyrimidin-4-one;

2-(4-Fluoro-phenylamino)-3-methyl-5-[5-(7,8,10,11-tetrahydro-6,9,12-trioxa-1-aza-cyclonona[b]naphthalen-4-yloxy)-pyridin-2-yl]-3H-pyrimidin-4-one;

3-Methyl-2-phenylamino-5-[5-(2,5,7,10-tetraoxa-14-aza-tricyclo[9.8.0.013,18]nonadeca-1(11),12,14,16,18-pentaen-17-yloxy)-pyridin-2-yl]-3H-pyrimidin-4-one;

5-[5-(2,2-Difluoro-[1,3]dioxolo[4,5-g]quinolin-8-yloxy)-pyridin-2-yl]-2-(2-fluoro-phenylamino)-3-methyl-3H-pyrimidin-4-one;

5-[5-(2,2-Difluoro-[1,3]dioxolo[4,5-g]quinolin-8-yloxy)-pyridin-2-yl]-2-(phenylamino)-3-methyl-3H-pyrimidin-4-one;

5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1,3-diaza-cyclododeca[b]naphthalen-4-ylamino)-phenyl]-amide;

5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1,3-diaza-cyclododeca[b]naphthalen-4-ylsulfanyl)-phenyl]-amide;

5-[5-(2,5,8,11,14,17-Hexaoxa-21-aza-tricyclo[16.8.0.020,25]hexacosa-1(18),19,21,23,25-pentaen-24-yloxy)-pyridin-2-yl]-3-methyl-2-phenylamino-3H-pyrimidin-4-one.

In another aspect, the present invention is directed to a pharmaceutical composition, comprising: at least one of the above compound and a pharmaceutically acceptable excipient. The term "pharmaceutically acceptable excipient" refers to any of a diluent, adjuvant, excipient or carrier with which at least one compound of the present disclosure is administered.

The present invention provides also the optimization of technical solutions of above-mentioned technical solutions.

The said compound is in a weight ratio to the said excipient within the range from about 0.0001 to about 10:1.

The present invention provides further the use of above the pharmaceutical composition and at least one compound shown as formula I to preparation of a medicament.

The present invention provides also the optimization of technical solutions of above-mentioned the use.

The use for the preparation of a medicament is for the treatment or prevention of cancer, cancer metastasis, cardiovascular disease, an immunological disorder or an ocular disorder.

The use for the preparation of a medicament is for delaying or preventing disease progression in cancer, cancer metastasis, cardiovascular disease, an immunological disorder or an ocular disorder.

The use for the preparation of a medicament is for treating or delaying the progression or onset of cancer, cancer metastasis, cardiovascular disease, an immunological disorder or an ocular disorder.

The present invention provides a compound for use shown as formula I, which is for use in the treatment of cancer, the prevention of cancer metastasis or the treatment of cardiovascular disease, an immunological disorder or an ocular disorder.

As preferred, the compound use as an inhibitor of c-Met, of at least one compound.

The present invention provides a method of treating a patient having a condition which is mediated by protein kinase activity, said method comprising administering to the patient a therapeutically effective amount of a compound shown as formula I or a pharmaceutically acceptable salt thereof.

As preferred, the protein kinase is KDR, Tie-2, Flt3, FGFR3, AbI, Aurora A, c-Src, IGF-IR, ALK, c-MET, RON, PAK1, PAK2, or TAK1.

As preferred, the said condition mediated by protein kinase activity is cancer.

As preferred, the said cancer is a solid tumor, a sarcoma, fibrosarcoma, osteoma, melanoma, retinoblastoma, a rhabdomyosarcoma, glioblastoma, neuroblastoma, teratocarcinoma, a hematopoietic malignancy, or malignant ascites.

The present invention provides also the compound shown as formula I or a pharmaceutically acceptable salt thereof for use as a medicament.

As preferred, the said medicament is use in the treatment of cancer.

As preferred, the said cancer selected from the group consisting of lung cancer, breast cancer, colorectal cancer, renal cancer, pancreatic cancer, head cancer, neck cancer, hereditary papillary renal cell carcinoma, childhood hepatocellular carcinoma, and gastric cancer in a mammal comprising administering to a mammal in need of such treatment an effective amount of a compound of this invention or a pharmaceutically acceptable salt thereof.

In another aspect, the present invention is directed to a method of treating a patient suffering from c-Met tyrosine kinase-mediated disorders, comprising the step of administering to said patient a therapeutically effective amount of the compound of the above compound.

The term "halo" or "halogen", as used herein, unless otherwise indicated, means fluoro, chloro, bromo or iodo. Preferred halo groups are fluoro, chloro and bromo.

As used herein, unless otherwise indicated, alkyl includes saturated monovalent hydrocarbon radicals having straight, branched or cyclic moieties. For example, alkyl radicals include methyl, ethyl, propyl, isopropyl, cyclcopropyl, n-butyl, isobutyl, sec-butyl, t-butyl, cyclcobutyl, n-pentyl, 3-(2-methyl)butyl, 2-pentyl, 2-methylbutyl, neopentyl, cyclcopentyl, n-hexyl, 2-hexyl, 2-methylpentyl and cyclohexyl. Alkoxy radicals are oxygen ethers formed from the previously described straight, branched chain or cyclic alkyl groups. Similarly, alkenyl and alkynyl groups include straight, branched chain or cyclic alkenes and alkynes.

The term "hydroxyalkyl" refers to radicals wherein the alkyl chain terminates with a hydroxy radical of the formula HO-alkyl. The term "aminoalkyl" refers to an alkyl group substituted with an amino group (i.e., -alkyl-$NH_2$). The term "alkylamino" refers to an amino group substituted with an alkyl group (i.e., —NH-alkyl). The term "dialkylamino" refers to an amino group which is disubstituted with alkyl groups wherein the alkyl groups can be the same or different (i.e., —N-$[alkyl]_2$).

The term "aryl", as used herein, unless otherwise indicated, refers to an unsubstituted or substituted aromatic group such as phenyl, naphthyl and anthracenyl. The term "aroyl" refers to the group —C(O)-aryl.

The term "heterocyclyl", as used herein, unless otherwise indicated, represents an unsubstituted or substituted stable three to eight membered monocyclic saturated ring system which consists of carbon atoms and from one to three heteroatoms selected from N, O or S, and wherein the nitrogen or sulfur heteroatoms may optionally be oxidized, and the nitrogen heteroatom may optionally be quaternized. The heterocyclyl group may be attached at any heteroatom or carbon atom which results in the creation of a stable structure. Examples of such heterocyclyl groups include, but are not limited to azetidinyl, pyrrolidinyl, piperidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl.

The term "heteroaryl", as used herein, unless otherwise indicated, represents an unsubstituted or substituted stable five or six membered monocyclic aromatic ring system or an unsubstituted or substituted nine or ten membered benzo-fused heteroaromatic ring system or bicyclic heteroaromatic ring system which consists of carbon atoms and from one to four heteroatoms selected from N, O or S, and wherein the nitrogen or sulfur heteroatoms may optionally be oxidized, and the nitrogen heteroatom may optionally be quaternized. The heteroaryl group may be attached at any heteroatom or carbon atom which results in the creation of a stable structure. Examples of heteroaryl groups include, but are not limited to thienyl, furanyl, imidazolyl, isoxazolyl, oxazolyl, pyrazolyl, pyrrolyl, thiazolyl, thiadiazolyl, triazolyl, pyridyl, pyridazinyl, indolyl, azaindolyl, indazolyl, benzimidazolyl, benzofuranyl, benzothienyl, benzisoxazolyl, benzoxazolyl, benzopyrazolyl, benzothiazolyl, benzothiadiazolyl, benzotriazolyl adeninyl, quinolinyl or isoquinolinyl.

The term "arylalkyl" means an alkyl group substituted with one or more aryl groups.

The "arylalkenyl" or "arylalkynyl" indicates an alkenyl or alkynyl group substituted with one or more aryl groups. Similarly, the "heteroarylalkyl", "heteroarylalkenyl" or "heteroarylalkynyl" means an alkyl, alkenyl or alkynyl group substituted with one or more heteroaryl groups, and "heterocyclylalkyl", "heterocyclylallcenyl" or "heterocyclylalkynyl" means an alkyl, alkenyl or alkynyl group substituted with one or more heterocyclyl groups.

The term "carbonyl" refers to the group C(O).

Whenever the term "alkyl" or "aryl" or either of their prefix roots appear in a name of a substituent (e.g., aralkyl, dialkylamino) it shall be interpreted as including those limitations given above for "alkyl" and "aryl". Designated numbers of carbon atoms (e.g., $C_1$-$C_6$) shall refer independently to the number of carbon atoms in an alkyl moiety or to the alkyl portion of a larger substituent in which alkyl appears as its prefix root.

The term "composition", as used herein, is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention. Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

The compounds of the present invention may also be present in the form of pharmaceutically acceptable salts. For use in medicine, the salts of the compounds of this invention refer to non-toxic "pharmaceutically acceptable salts". The pharmaceutically acceptable salt forms include pharmaceutically acceptable acidic/anionic or basic/cationic salts. The pharmaceutically acceptable acidic/anionic salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salkylic, saccharinic or trifluoroacetic. Pharmaceutically acceptable basic/cationic salts include, and are not limited to aluminum, calcium, chloroprocaine, choline, diethanolamine, ethylenediamine, lithium, magnesium, potassium, sodium and zinc.

The present invention includes within its scope the prodrugs of the compounds of this invention. In general, such prodrugs will be functional derivatives of the compounds that are readily converted in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

The present invention includes compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof.

The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or cpimerization procedures known to those skilled in the art, the products of such procedures can be a mixture of stereoisomers.

When a tautomer of the compound of Formula (I) exists, the present invention includes any possible tautomers and pharmaceutically acceptable salts thereof, and mixtures thereof, except where specifically stated otherwise.

When the compound of Formula (I) and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, formic, hydrochloric, maleic, phosphoric, sulfuric and tartaric acids. Particularly preferred are formic and hydrochloric acid. Since the compounds of Formula (I) are intended for pharmaceutical use they are preferably provided in substantially pure form, for example at least 60% pure, more suitably at least 75% pure especially at least 98% pure (% are on a weight for weight basis).

The pharmaceutical compositions of the present invention comprise a compound represented by Formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or a prodrug, or a metabolite, or a pharmaceutically acceptable salt thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound, or a pharmaceutically acceptable salt, of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the central nervous system (CNS), may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

These and other aspects will become apparent from the following written description of the invention.

DETAILED DESCRIPTION OF THE INVENTION

The present invention is directed to novel compounds having c-Met inhibitory activity. The compounds of the invention have the general structure as Formula I:

formula I wherein

A is a 5-18 membered ring;

$R_1$ is selected from the group consisting of hydrogen, halogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alkynyloxy, $C_{1-8}$alkylthio, carbamoyl, N, carbamoyl, $C_{1-8}$alkanoyloxy, $C_{1-8}$alkanoylamino, $C_{3-8}$alkynoylamino, N—($C_{1-8}$alkyl) sulfamoyl, and N, N-di($C_{1-8}$alkyl) sulfamoyl;

m is an integer from 0 to 3;

$A_1$ and $A_2$ are each independently selected from =N—, =C($R_2$)—;

$A_3$ is selected from =N—, =C(H)—, and =C(CN)—;

X is selected from the group consisting of $NR_{20}$, $CHR_{21}$, O, or S; wherein $R_{20}$ and $R_{21}$ are each independently H or $C_{1-8}$alkyl;

$R_2$ is selected from —H, halogen, trihalomethyl, —CN, —$NO_2$, —$NH_2$, —$OR_5$, —$NR_5R_6$, —$S(O)_{0-2}R_5$, —$SO_2NR_5R_6$, —$CO_2R_5$, —$C(O)NR_5R_6$, —$N(R_3)SO_2R_5$, —$N(R_5)C(O)R_6$, —$N(R_5)CO_2R_6$, —$C(O)R_5$, and optionally substituted lower alkyl;

n is 0 to 4;

Z is selected from $NR_3R_4$ or group having Formula II

Formula II $R_3$ is independent selected from the group consisting of hydrogen, substituted or unsubstituted $C_{1-8}$alkyl, substituted or unsubstituted $C_{2-8}$alkenyl, substituted or unsubstituted $C_{2-8}$alkynyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alkynyloxy, $C_{1-8}$alkylthio, N—($C_{1-8}$alkyl) carbamoyl, N, N-di($C_{1-8}$alkyl) carbamoyl, $C_{1-8}$alkanoyloxy, $C_{1-8}$alkanoylamino, $C_{3-8}$alkynoylamino, N—($C_{1-8}$alkyl) sulfamoyl, and N,N-di($C_{1-8}$alkyl) sulfamoyl;

$R_4$ is selected from the group having Formula III:

Formula III $B_1$ is $Q_1$ is $C(R_5)_2$;

$B_2$ is $NHQ_2$;

$Q_2$ is selected from the group consisting of substituted or unsubstituted aryl, substituted or unsubstituted heteroaryl, substituted or unsubstituted heterocyclyl, substituted or unsubstituted $C_{1-8}$alkylaryl, substituted or unsubstituted $C_{1-8}$alkylheteroaryl, substituted or unsubstituted $C_{1-8}$alkylheterocyclyl;

$B_1$ and $B_2$ together may form 5 to 10 member substituted or unsubstituted heteroaryl, substituted or unsubstituted heterocyclyl;

$R_5$ and $R_6$ are each independently selected from the group consisting of hydrogen, halogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alkynyloxy, $C_{1-8}$alkylthio, N—($C_{1-8}$alkyl) carbamoyl, N, N-di($C_{1-8}$alkyl) carbamoyl, $C_{1-8}$alkanoyloxy, $C_{1-8}$alkanoylamino, $C_{3-8}$alkynoylamino, N—($C_{1-8}$alkyl) sulfamoyl, and N, N-di($C_{1-8}$alkyl) sulfamoyl; substituted or unsubstituted $C_{1-8}$alkylaryl, substituted or unsubstituted $C_{1-8}$alkylheteroaryl, or unsubstituted $C_{1-8}$alkylheterocyclyl; and pharmaceutically acceptable salts thereof;

In one preferred embodiment, ring A further comprises 0 to 6 heteroatoms selected from the group consisting of O, S, and N.

In a preferred embodiment, $R_1$ is selected from the group consisting hydrogen, halogen, $C_{1-8}$alkyl, $C_{2-8}$alkenyl, $C_{2-8}$alkynyl, aryl, heteroaryl, heterocyclyl, (halo)$_{1-3}$($C_{1-8}$) alkyl, hydroxy ($C_{1-8}$)alkyl, $C_{1-8}$alkoxy($C_{1-8}$) alkyl, cyano ($C_{1-8}$) alkyl, amino ($C_{1-8}$)alkyl, aryl ($C_{1-8}$) alkyl, heteroaryl ($C_{1-8}$) alkyl, heterocyclyl ($C_{1-8}$) alkyl, (halo)$_{1-3}$($C_{2-8}$) alkenyl, hydroxy($C_{2-8}$)alkenyl, ($C_{1-4}$ alkoxy($C_{2-8}$)alkenyl, cyano ($C_{2-8}$)alkenyl, and amino($C_{2-8}$)alkenyl, aryl($C_{2-8}$)alkenyl, heteroaryl($C_{2-8}$)alkenyl, heterocyclyl($C_{2-8}$)alkenyl, (halo)$_{1-3}$ ($C_{2-8}$)alkynyl, hydroxy($C_{2-8}$)alkynyl, $C_{1-4}$alkoxy($C_{2-8}$)alkynyl, cyano($C_{2-8}$)alkynyl, amino($C_{2-8}$)alkynyl, aryl($C_{2-8}$)alkynyl, heteroaryl ($C_{2-8}$)alkynyl, heterocyclyl($C_{2-8}$)alkynyl, $C_{1-8}$alkanoyl, aryl($C_{1-8}$)alkanoyl, heteroaryl($C_{1-8}$) alkanoyl, heterocyclyl($C_{1-8}$)alkanoyl, $C_{1-8}$alkoxycarbonyl, aryl($C_{1-8}$) alkoxycarbonyl, heteroaryl($C_{1-8}$)alkoxycarbonyl, heterocyclyl($C_{1-8}$)alkoxycarbonyl, $C_{1-8}$alkylsulfinyl, $C_{1-8}$alkylsulfonyl, arylsulfonyl, aryl($C_{1-8}$)alkylsulfonyl, heteroaryl($C_{1-8}$) alkylsulfonyl, heterocyclyl($C_{1-8}$) alkylsulfonyl, aryl, heteroaryl, heterocyclyl, cyano, nitro, hydroxy, amino, carboxy, oxo, carbamoyl, $C_{1-8}$alkoxy, $C_{2-8}$alkenyloxy, $C_{2-8}$alkynyloxy, $C_{1-8}$alkylthio, N—($C_{1-8}$alkyl) carbamoyl, carbamoyl, $C_{1-8}$alkanoyloxy, $C_{1-8}$alkanoylamino, $C_{3-8}$alknoylamino, N—($C_{1-8}$alkyl) sulfamoyl, and N,N-di-($C_{1-8}$alkyl) sulfamoyl.

In another preferred embodiment, the above amino, amino ($C_{1-8}$)alkyl, amino($C_{2-8}$) alkenyl or amino($C_{2-8}$) alkynyl within $R_1$ is substituted with two substituents independently selected from the group consisting of hydrogen, $C_{1-8}$alkyl, $C_{2-8}$alkenyl, $C_{2-8}$alkynyl.

In another preferred embodiment, any aryl, heteroaryl or heterocyclyl group within optionally bears one to three substituents independently selected from halogeno, trifluoromethyl, cyano, nitro, hydroxy, amino, carboxy, carbamoyl, ($C_{1-8}$)alkyl, ($C_{2-8}$)alkenyl, ($C_{2-8}$)alkynyl, ($C_{1-8}$)alkoxy.

In another preferred embodiment, $R_3$ is independent selected from the group consisting of hydrogen, substituted or unsubstituted $C_{1-8}$alkyl, substituted or unsubstituted $C_{2-8}$alkenyl, substituted or unsubstituted $C_{2-8}$alkynyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alknyloxy, $C_{1-8}$alkylthio, N—($C_{1-8}$alkyl) carbamoyl, N, N-di($C_{1-8}$alkyl) carbamoyl, $C_{1-8}$alkanoyloxy, $C_{1-8}$alkanoylamino, $C_{3-8}$alkynoylamino, N—($C_{1-8}$alkyl) sulfamoyl, and N, N-di ($C_{1-8}$alkyl) sulfamoyl;

In another preferred embodiment, $R_4$ is selected from the group having Formula IV:

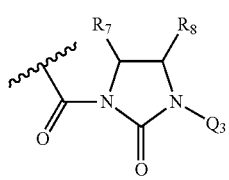

Formula IV wherein $Q_3$ is selected from the group consisting of substituted or unsubstituted aryl, substituted or unsubstituted heteroaryl, substituted or unsubstituted heterocyclyl, substituted or unsubstituted $C_{1-8}$alkylaryl, substituted or unsubstituted $C_{1-8}$alkylheteroaryl, substituted or unsubstituted $C_{1-8}$alkylheterocyclyl;

$R_7$ and $R_8$ are each independently selected from the group consisting of hydrogen, halogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alknyloxy, $C_{1-8}$alkylthio, N—($C_{1-8}$alkyl) carbamoyl, N, N-di($C_{1-8}$alkyl) carbamoyl, $C_{1-8}$alkanoyloxy, $C_{1-8}$alkanoylamino, $C_{3-8}$alkynoylamino, N—($C_{1-8}$alkyl) sulfamoyl, and N, N-di($C_{1-8}$alkyl) sulfamoyl; substituted or unsubstituted $C_{1-8}$alkylaryl, substituted or unsubstituted $C_{1-8}$alkylheteroaryl, substituted or unsubstituted $C_{1-8}$alkylheterocyclyl;

In another preferred embodiment, $R_3$ is independent selected from the group consisting of hydrogen, substituted or unsubstituted $C_{1-8}$alkyl, substituted or unsubstituted $C_{2-8}$alkenyl, substituted or unsubstituted $C_{2-8}$alkynyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alkynyloxy, $C_{1-8}$alkylthio, N—($C_{1-8}$alkyl) carbamoyl, N,N-di($C_{1-8}$alkyl) carbamoyl, $C_{1-8}$alkanoyloxy, $C_{1-8}$alkanoylamino, $C_{3-8}$alkynoylamino, N—($C_{1-8}$alkyl) sulfamoyl, and N, N-di ($C_{1-8}$alkyl) sulfamoyl;

In another preferred embodiment, $R_4$ is selected from the group having Formula V:

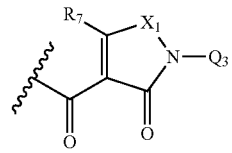

Formula V wherein $Q_3$ is selected from the group consisting of substituted or unsubstituted aryl, substituted or unsubstituted heteroaryl, substituted or unsubstituted heterocyclyl, substituted or unsubstituted $C_{1-8}$alkylaryl, substituted or unsubstituted $C_{1-8}$alkylheteroaryl, substituted or unsubstituted $C_{1-8}$alkylheterocyclyl;

$X_1$ is selected from the group consisting of $NR_R$, $CR_7R_8$;

$R_7$ and $R_8$ are each independently selected from the group consisting of hydrogen, halogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alknyloxy, $C_{1-8}$alkylthio, N—($C_{1-8}$alkyl) carbamoyl, N, N-di($C_{1-8}$alkyl) carbamoyl, $C_{1-8}$alkanoyloxy, $C_{1-8}$alkanoylamino, $C_{3-8}$alkynoylamino, N—($C_{1-8}$alkyl) sulfamoyl, and N, N-di($C_{1-8}$alkyl) sulfamoyl; substituted or unsubstituted $C_{1-8}$alkylaryl, substituted or unsubstituted $C_{1-8}$alkylheteroaryl, substituted or unsubstituted $C_{1-8}$alkylheterocyclyl;

In another preferred embodiment, $R_3$ is independent selected from the group consisting of hydrogen, substituted or unsubstituted $C_{1-8}$alkyl, substituted or unsubstituted $C_{2-8}$alkenyl, substituted or unsubstituted $C_{2-8}$alkynyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alkynyloxy, $C_{1-8}$alkylthio, N—($C_{1-8}$alkyl) carbamoyl, N,N-di($C_{1-8}$alkyl) carbamoyl, $C_{1-8}$alkanoyloxy, $C_{1-8}$alkanoylamino, $C_{3-8}$alkynoylamino, N—($C_{1-8}$alkyl) sulfamoyl, and N, N-di ($C_{1-8}$alkyl) sulfamoyl;

In another preferred embodiment, $R_4$ is selected from the group having Formula VI:

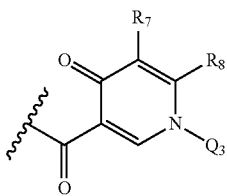

Formula VI wherein

Q₃ is selected from the group consisting of substituted or unsubstituted aryl, substituted or unsubstituted heteroaryl, substituted or unsubstituted heterocyclyl, substituted or unsubstituted $C_{1-8}$alkylaryl, substituted or unsubstituted $C_{1-8}$alkylheteroaryl, substituted or unsubstituted $C_{1-8}$alkylheterocyclyl;

R₇ and R₈ are each independently selected from the group consisting of hydrogen, halogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, $C_{1-8}$alkoxycarbonyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alknyloxy, $C_{1-8}$alkylthio, N—($C_{1-8}$alkyl) carbamoyl, N, N-di($C_{1-8}$alkyl) carbamoyl, $C_{1-8}$alkanoyloxy, $C_{1-8}$alkanoylamino, $C_{1-8}$alkynoylamino, N—($C_{1-8}$alkyl) sulfamoyl, and N, N-di($C_{1-8}$alkyl) sulfamoyl; substituted or unsubstituted $C_{1-8}$alkylaryl, substituted or unsubstituted $C_{1-8}$alkylheteroaryl, substituted or unsubstituted $C_{1-8}$alkylheterocyclyl;

In another preferred embodiment, R₄ is selected from the group having Formula VII:

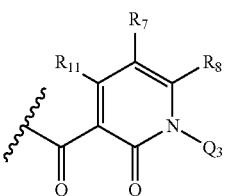

Formula VII wherein

Q₃ is selected from the group consisting of substituted or unsubstituted aryl, substituted or unsubstituted heteroaryl, substituted or unsubstituted heterocyclyl, substituted or unsubstituted $C_{1-8}$alkylaryl, substituted or unsubstituted $C_{1-8}$alkylheteroaryl, substituted or unsubstituted $C_{1-8}$alkylheterocyclyl;

R₇, R₈ and R₁₁ are each independently selected from the group consisting of hydrogen, halogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alknyloxy, $C_{1-8}$alkylthio, N—($C_{1-8}$alkyl) carbamoyl, N, N-di($C_{1-8}$alkyl) carbamoyl, $C_{1-8}$alkanoyloxy, $C_{1-8}$alkanoylamino, $C_{3-8}$alkynoylamino, N—($C_{1-8}$alkyl) sulfamoyl, and N, N-di ($C_{1-8}$alkyl) sulfamoyl; substituted or unsubstituted $C_{1-8}$alkylaryl, substituted or unsubstituted $C_{1-8}$alkylheteroaryl, substituted or unsubstituted $C_{1-8}$alkylheterocyclyl;

R₉ and R₁₀ are each independently selected from the group consisting of substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, $C_{1-8}$alkoxycarbonyl, $C_{1-8}$alkylsulfinyl, $C_{1-8}$alkylsulfonyl, arylsulfonyl;

The compounds of Formula I inhibit the activity of tyrosine kinase enzymes in animals, including humans, and they are useful in the treatment and/or prevention of various diseases and conditions. In particular, compounds disclosed herein are inhibitors of kinases, in particular, but not limited to, c-MET, KDR, Tie-2, Flt3, FGFR3, AbI, Aurora A, c-Src, IGF-IR, ALK, c-MET, RON, PAK1, PAK2, and TAK1, and can be used in the treatment of proliferative diseases, such as, but not limited to, cancer. Since MET and RON kinases have been shown to play a role in the EMT process, the compounds of Formula I are useful in the treatment and/or prevention of various diseases and conditions in which EMT is involved, for example, the treatment of conditions characterized by a disregulation of EMT.

Specifically, the compounds of Formula I of the present invention are useful in the treatment of a variety of cancers, including, but not limited to, solid tumor, sarcoma, fibrosarcoma, osteoma, melanoma, retinoblastoma, rhabdomyosarcoma, glioblastoma, neuroblastoma, teratocarcinoma, hematopoictic malignancy, and malignant ascites. More specifically, the cancers include, but not limited to, lung cancer, bladder cancer, pancreatic cancer, kidney cancer, gastric cancer, breast cancer, colon cancer, prostate cancer (including bone metastases), hepatocellular carcinoma, ovarian cancer, esophageal squamous cell carcinoma, melanoma, an anaplastic large cell lymphoma, an inflammatory myofibroblastic tumor, and a glioblastoma.

In another embodiment, the present invention is directed to a pharmaceutical composition comprising a therapeutically effective amount of a compound of Formula I, or a pharmaceutically acceptable salt thereof, and a pharmaceutically acceptable carrier. The present invention is also directed to a method of treating a patient having a condition which is mediated by protein kinase activity by administering to the patient a therapeutically effective amount of the above-mentioned pharmaceutical composition.

The flowing compounds of the invention are provided to give the reader an understanding of the compounds encompassed by the invention:

(1). 5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1,3-diaza-cyclododeca[b]naphthalen-4-yloxy)-phenyl]-amide;

(2). 1-(4-Fluoro-phenyl)-2-oxo-1,2-dihydro-pyridine-3-carboxylic acid [3-fluoro-4-(7,8,10,11,13,14-hexahydro-6,9,12,15-tetraoxa-1,3-diaza-cyclododeca[b]naphthalen-4-yloxy)-phenyl]-amide;

(3). Cyclopropane-1,1-dicarboxylic acid[3-fluoro-4-(7,8,10,11,13,14-hexahydro-6,9,12,15-tetraoxa-1,3-diaza-yclododeca[b]naphthalen-4-yloxy)-phenyl]-amide (4-fluoro-phenyl)-amide;

(4). 3-(4-Fluoro-phenyl)-2-oxo-imidazolidine-1-carboxylic acid [3-fluoro-4-(7,8,10,11,13,14-hexahydro-6,9,12,15-tetraoxa-1,3-diaza-cyclododeca[b]naphthalen-4-yloxy)-phenyl]-amide;

(5). 2-(4-Fluoro-phenyl)-1,5-dimethyl-3-oxo-2,3-dihydro-1H-pyrazole-4-carboxylic acid [3-fluoro-4-(7,8,10,11,13, (6). 2-(4-Fluoro-phenylamino)-5-[5-(7,8,10,11,13,14-hexahydro-6,9,12,15-tetraoxa-1,3-diaza-cyclododeca[b]naphthalen-4-yloxy)-pyridin-2-yl]-3-methyl-3H-pyrimidin-4-one;

(7). 5-[5-([1,3]Dioxolo[4,5-g]quinazolin-8-yloxy)-pyridin-2-yl]-2-(4-fluoro-phenylamino)-3-methyl-3H-pyrimidin-4-one;

(8). 5-[5(2,2-Difluoro-[1,3]dioxolo[4,5-g]quinazolin-8-yloxy)-pyridin-2-yl]-2-(4-fluoro-phenylamino)-3-methyl-3H-pyrimidin-4-one;

(9). 5-(4-Fluoro-phenyl)-4-oxo-1,4-dihydro-pyridine-3-carboxylic acid [4-([1,3]dioxolo[4,5-g]quinazolin-8-yloxy)-3-fluoro-phenyl]-amide;

(10). 5-(4-Fluoro-phenyl)-4-oxo-1,4-dihydro-pyridine-3-carboxylic acid [3-fluoro-4(7,8,10,11,13,14-hexahydro-6,9,12,15-tetraoxa-1-aza-cyclododeca[b]naphthalen-4-yloxy)-phenyl]-amide;

(11). 1-(4-Fluoro-phenyl)-2-oxo-1,2-dihydro-pyridine-3-carboxylic acid [3-fluoro-4-(7,8,10,11,13,14-hexahydro-6,9,12,15-tetraoxa-1-aza-cyclododeca[b]naphthalen-4-yloxy)-phenyl]-amide;

(12). 2-(4-Fluoro-phenyl)-1,5-dimethyl-3-oxo-2,3-dihydro-1H-pyrazole-4-carboxylic acid [3-fluoro-4(7,8,10,11,13,14-hexahydro-6,9,12,15-tetraoxa-1-aza-cyclododeca[b]naphthalen-4-yloxy)-phenyl]-amide;

(13). Cyclopropane-1,1-dicarboxylic acid[3-fluoro-4-(7,8,10,11,13,14-hexahydro-6,9,12,15-tetraoxa-1-aza-cyclododeca[b]naphthalen-4-yloxy)-phenyl]-amide (4-fluoro-phenyl)-amide;

(14). 3-(4-Fluoro-phenyl)-2-oxo-imidazolidine-1-carboxylic acid [3-fluoro-4-(7,8,10,11,13,14-hexahydro-6,9,12,15-tetraoxa-1-aza-cyclododeca[b]naphthalen-4-yloxy)-phenyl]-amide;

(15). 5-[5-(2,2-Difluoro-[1,3]dioxolo[4,5-g]quinazolin-8-yloxy)-pyridin-2-yl]-2-(2-fluoro-phenylamino)-3-methyl-3H-pyrimidin-4-one;

(16). 5-[5-(2,2-Difluoro-[1,3]dioxolo[4,5-g]quinazolin-8-yloxy)-pyridin-2-yl]-2-(phenylamino)-3-methyl-3H-pyrimidin-4-one;

(17). 5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1-aza-cyclododeca[b]naphthalen-4-ylamino)-phenyl]-amide;

(18). 5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1-aza-cyclododeca[b]naphthalen-4-ylsulfanyl)-phenyl]-amide;

(19). 3-Methyl-2-phenylamino-5-[5-(2,5,7,10-tetraoxa-14,16-diaza-tricyclo[9.8.0.013,18]nonadeca-1(11),12,14,16,18-pentaen-17-yloxy)-pyridin-2-yl]-3H-pyrimidin-4-one;

(20). 5-[5-(8,9-Dihydro-7H-6,10-dioxa-1,3-diaza-cyclohepta[b]naphthalen-4-yloxy)-pyridin-2-yl]-2-(4-fluoro-phenylamino)-3-methyl-3H-pyrimidin-4-one;

(21). 2-(4-Fluoro-phenylamino)-3-methyl-5-[5-(9-methyl-8,9,10,11-tetrahydro-7H-6,12-dioxa-1,3,9-triaza-cyclonona[b]naphthalen-4-yloxy)-pyridin-2-yl]-3H-pyrimidin-4-one;

(22). 2-(4-Fluoro-phenylamino)-3-methyl-5-[5-(7,8,10,11-tetrahydro-6,9,12-trioxa-1,3-diaza-cyclonona[b]naphthalen-4-yloxy)-pyridin-2-yl]-3H-pyrimidin-4-one;

(23). 5-[5-(8,9-Dihydro-7H-6,10-dioxa-1-aza-cyclohepta[b]naphthalen-4-yloxy)-pyridin-2-yl]-2-(4-fluoro-phenylamino)-3-methyl-3H-pyrimidin-4-one;

(24). 2-(4-Fluoro-phenylamino)-3-methyl-5-[5-(9-methyl-8,9,10,11-tetrahydro-7H-6,12-dioxa-1,9-diaza-cyclonona[b]naphthalen-4-yloxy)-pyridin-2-yl]-3H-pyrimidin-4-one;

(25). 2-(4-Fluoro-phenylamino)-3-methyl-5-[5-(7,8,10,11-tetrahydro-6,9,12-trioxa-1-aza-cyclonona[b]naphthalen-4-yloxy)-pyridin-2-yl]-3H-pyrimidin-4-one;

(26). 3-Methyl-2-phenylamino-5-[5-(2,5,7,10-tetraoxa-14-aza-tricyclo[9.8.0.013,18]nonadeca-1(11),12,14,16,18-pentaen-17-yloxy)-pyridin-2-yl]-3H-pyrimidin-4-one;

(27). 5-[5-(2,2-Difluoro-[1,3]dioxolo[4,5-g]quinolin-8-yloxy)-pyridin-2-yl]-2-(2-fluoro-phenylamino)-3-methyl-3H-pyrimidin-4-one;

(28). 5-[5-(2,2-Difluoro-[1,3]dioxolo[4,5-g]quinolin-8-yloxy)-pyridin-2-yl]-2-(phenylamino)-3-methyl-3H-pyrimidin-4-one;

(29). 5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1,3-diaza-cyclododeca[b]naphthalen-4-ylamino)-phenyl]amide;

(30). 5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1,3-diaza-cyclododeca[b]naphthalen-4-ylsulfanyl)-phenyl]-amide;

(31). 5-[5-(2,5,8,11,14,17-Hexaoxa-21-aza-tricyclo[16.8.0.020,25]hexacosa-1(18), 19,21,23,25-pentaen-24-yloxy)-pyridin-2-yl]-3-methyl-2-phenylamino-3H-pyrimidin-4-one.

As defined herein, the term "subject" refers to an animal, preferably a mammal, most preferably a human, who has been the object of treatment, observation or experiment. The term "therapeutically effective amounts" used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "substituted", as defined herein, includes multiple substituents (e.g., Phe, aryl, heteroalkyl, heteroaryl), preferably from one to five substituents, more preferably from one to three substituents, most preferably from one to two substituents, independently selected from the list of substituents.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereornric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

In general, the compounds of the present invention can be prepared according to Scheme 1 depicts general synthetic routes for compounds of the invention and are not intended to be limiting. More specifically, Scheme 1 depicts synthesis of quinazoline compounds, and quinoline compounds. Specific examples are described subsequently to these general synthetic descriptions so as to allow one skilled in the art to make and use either quinazolines or quinolines of the invention.

Scheme 1 outlines the general procedures one could use to provide compounds of the present invention, for example Z is NR$_3$R$_4$ in formula I.

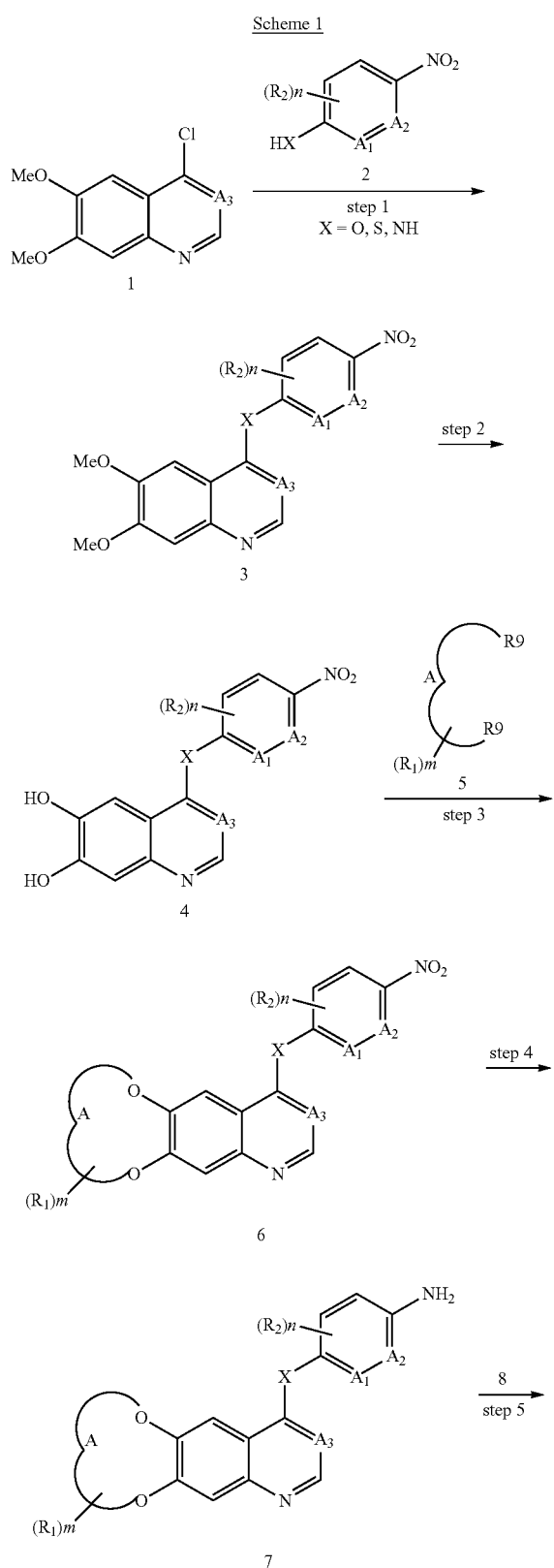

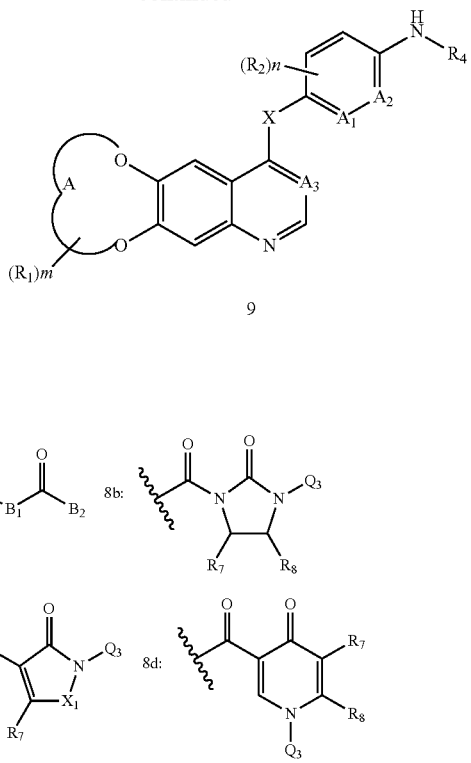

4-Chloro-6,7-dimethoxy-quinazoline (1a) or 4-chloro-6,7-dimethoxy-quinoline (1b) is commercial available or been prepared by conventional methods known by those skilled in the art. In step 1 of Scheme 1, nucleophilic substitution of 1a or 1b with anilines 2a, phenols 2b or thiophenols 2c can be easily accomplished in the presence of a trialkylamine or alkali carbonation (e.g., triethylamine, potassium carbonate).

In step 2 of Scheme 1, both methyl protecting groups of intermediate 3 in 6 and 7 position are removed by treating the intermediate from step 1 with the appropriate reagents and procedures. For example, boron tribromide is at 0° C. for 1 hr and following 4 hrs at room temperature.

In step 3 of Scheme 1, the fused heterocyclic ring is prepared by treatment of the diphenol intermediate 4 with the appropriate reagents such as 5 (the leaving group R$_9$ is tosylate, bromide or iodidate) with the existence of an trialkylamine or alkali carbonation (e.g., triethylamine, potassium carbonate). The selections of solvent and reaction temperature are important for high yields. DMF or DMSO would be a good choice as a solvent for this reaction.

In step 4 of Scheme 1, the reduction of nitro group is accomplished by hydrogenation using palladium on carbon as catalyst. Alternatively, Zinc powder or Iron powder reduction of nitro group also is available option.

The final step in Scheme 1, the final amides 9 can be prepared by coupling the aniline 7 with appropriate acids or corresponding acid chloride of 8 in the presence of base such as triethylamine, diisopropylethylamine. Coupling of aniline with acid 8 needs to use a coupling reagent, for example, HOBt, DCC.

Scheme 2

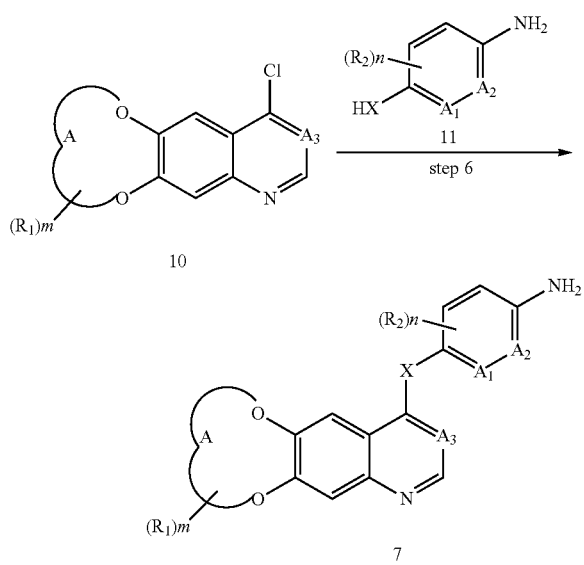

An alternative route for the key intermediates 7 is shown in Scheme 2. The coupling of 10 with anilines 11a, phenols 11b or thiophenols 11c yields the corresponding the key intermediates 7. The fused ring 4-Chloro-quinazoline (10a), 4-Chloro-quinoline (10b) or anilines 11a, phenols 11b or thiophenols 11c are commercial available, known in literature or may be conveniently prepared by a variety methods familiar to those skilled in the art.

Scheme 3

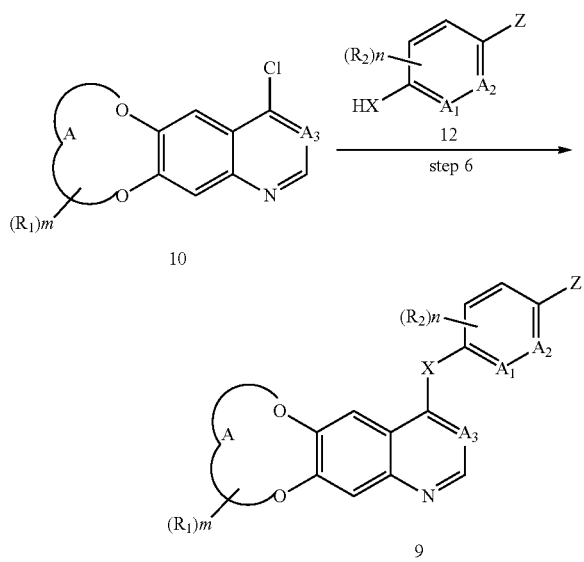

An alternative route for the final products of Formula I is shown in Scheme 3. The coupling of 10 with anilines 12a, phenols 12b or thiophenols 12c yields the corresponding compounds of Formula I. The fused ring 4-Chloro-quinazoline (10a), 4-chloro-quinoline (10b) or anilines 12a, phenols 12b or thiophenols 12c are commercial available, known in literature or may be conveniently prepared by a variety methods familiar to those skilled in the art.

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e. g. oral or parenteral). Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known in the art.

Administration of the active compounds can be effected by any method which enables delivery of the compounds to the site of action (e.g., cancer cells). These methods include oral routes, rectal routes, intraduodenal routes, parenteral injection (including intravenous, subcutaneous, intramuscular, intravascular or infusion), topical administration, etc. The amount of active compound administered will, of course, be dependent on the subject being treated, on the severity of the affliction, on the manner of administration and on the judgment of the prescribing physician. However an effective dosage is in the range of approximately 0.001 mg to about 300 mg (preferably, from about 0.01 mg to about 100 mg; and, more preferably, from about 0.1 mg to about 30 mg) and may be given at a dosage of from about 0.001 mg/kg/day to about 300 mg/kg/day (preferably, from about 0.01 mg/kg/day to about 100 mg/kg/day; and, more preferably, from about 0.1 mg/kg/day to about 30 mg/kg/day).

The composition may, for example, be in a form suitable for oral administration such as a tablet, capsule, pill, powder, sustained release formulation, solution, or suspension; for parenteral injection such as a sterile solution, suspension or emulsion; or for topical administration such as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the present invention as an active ingredient. In addition, it may include other medicinal or pharmaceutical agents, carriers, adjuvants, etc.

Exemplary parenteral administration forms include solutions or suspensions of active compounds in sterile aqueous solutions, for example aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes.

Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

An example of use of the invention is a method of treating a epidermal growth factor receptor (EGFR) tyrosine kinase or vascular endothelial growth factor receptor (VEGFR) tyrosine kinase mediated disorder in a subject in need thereof comprising administering to the subject a therapeutically effective amount of any of the compounds or pharmaceutical compositions described above. In a preferred embodiment, the method relates to the treatment of cancer such as brain, lung, squamous cell, bladder, gastric, pancreatic, breast, head, neck, oesophageal, prostate, colorectal, gynecological or thyroid cancer.

EXAMPLES

The following Examples are provided to better illustrate the present invention. All parts and percentages are by weight and all temperatures are degrees Celsius, unless explicitly stated otherwise. The following abbreviations have been used in the examples: ATP, Adenosine triphosphate; DMF, N,N-Dimethylformamide; DMSO, Dimethyl sulfoxide; EtOAc, Ethyl acetate; GSR, Glutathione-S-Transferase; Crk, CT10 (Chicken Tumor Retrovirus 10); min, Minute; h, Hour; rt, room temperature; SDS, Sodium Dodecyl Sulfate; SDS-PAGE, Sodium Dodecyl Sulfate PolyAcrylamide Electrophoresis Gel; TLC, Thin layer chromatography.

Example 1

5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1,3-diaza-cyclododeca[b]naphthalen-4-yloxy)-phenyl]-amide (9a)

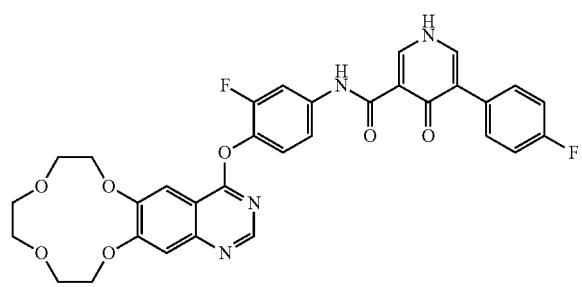 [SMILES: O=C(Nc1ccc(Oc2ncnc3cc4c(cc23)OCCOCCOCCO4)c(F)c1)c1c[nH]cc(-c2ccc(F)cc2)c1=O]

Step 1. 4-(4-Amino-2-Methyl-phenoxy)-7,8,10,11,13,14-hexahydro-6,9,12,15-tetraoxa-1,3-diaza-cyclododeca[b]naphthalene 4-amino-2-fluoro-phenol (1.53 g, 12.0 mmol) was dissolved in dry DMF (30 ml) to which was added 60% NaH (774 mg, 19.3 mmol). After the mixture was stirred at room temperature for several minutes, a suspension of 4-Chloro-7,8,10,11,13,14-hexahydro-6,9,12,15-tetraoxa-1,3-diaza-cyclododeca[b]naphthalene (2.08 g, 6.7 mmol) in dry DMF (40 ml) was added. The reaction mixture was stirred at room temperature for 1-2 hrs, then diluted with EtOAc and washed with sat'd NaHCO₃ (3×), H₂O (1×), sat'd NaCl (1×), dried (Na₂SO₄), and concentrated in vacuo to give crude title compound (2.68 g, ~100%) which was used in the next reaction without further purification. $^1$H-NMR (400 MHz, DMSO): 8.58 (s, 1H), 7.80 (s, 1H), 7.50 (s, 1H), 7.04 (t, 1H), 6.50 (dd, 2H), 5.40 (br s, 2H), 4.35 (s, 4H), 3.87 (d, 4H), 3.62 (s, 4H). LC/MS Calcd for (M+H)' 401.4. found 402.5.

Step 2. 5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1,3-diaza-cyclododeca[b]naphthalen-4-yloxy)-phenyl]-amide To a suspension of 5-(4-Fluorophenyl)-4-oxo-1,4-dihydropyridine-3-carboxylic acid 8d (J. Med. Chem. 2008, 51, 5330-5341) (8.0 g, 34.3 mmol) in anhydrous DMF (56 ml) were added HATU (15.65 g, 41.2 mmol) and i-Pr₂NEt (18 ml, 104 mmol) at ice bath temperature under nitrogen. The mixture turned into a clear solution after being stirred for 5 min. To the solution was added 4-(4-Amino-2-Methyl-phenoxy)-7,8,10,11,13,14-hexahydro-6,9,12,15-tetraoxa-1,3-diaza-cyclododeca[b]naphthalene 7a (7.9 g, 32.5 mmol) slowly. The reaction mixture was stirred for 3 h at room temperature and was poured into aqueous 1N HCl solution. The solid that formed was filtered, washed with distilled water, and dried. The crude product was purified by silica gel chromatography, eluting with 1-5% of MeOH in CH₂Cl₂ to obtain 9a as a light-yellow solid (5.9 g, 40%), mp 188-190° C. HPLC purity 97%; $^1$HNMR (400 MHz, DMSO) δ 13.13 (s, 1H), 12.68 (br s, 1H), 8.62 (m, 2H), 7.97-8.12 (m, 2H), 8.04-7.99 (m, 2H), 7.78 (m, 1H), 7.69 (m, 2H), 7.42 (d, 2H), 7.21 (m, 2H), 4.35 (s, 4H), 3.87 (d, 4H), 3.62 (s, 4H). LC/MS Calcd for (M+H)' 617.6. found 617.5.

Example 2

1-(4-Fluoro-phenyl)-2-oxo-1,2-dihydro-pyridine-3-carboxylic acid [3-fluoro-4-(7,8,10,11,13,14-hexahydro-6,9,12,15-tetraoxa-1,3-diaza-cyclododeca[b]naphthalen-4-yloxy)-phenyl]-amide

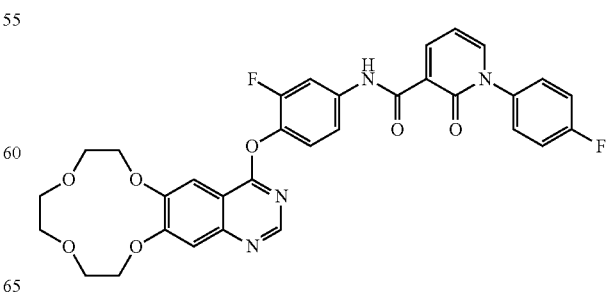

The desired title compound is synthesized by using the same sequence and conditions as described for Example 1 and 1-(4-Fluorophenyl)-2-oxo-1,2-dihydropyridine-3-carboxylic acid (J. Med. Chem. 2008, 51, 5330-5341) used instead of 5-(4-Fluorophenyl)-4-oxo-1,4-dihydro-pyridine-3-carboxylic acid. LC/MS Calcd for (M+H)' 617.6. found 617.5.

Example 3

Cyclopropane-1,1-dicarboxylic acid[3-fluoro-4-(7,8,10,11,13,14-hexahydro-6,9,12,15-tetraoxa-1,3-diaza-cyclododeca[b]naphthalen-4-yloxy)-phenyl]-amide (4-fluoro-phenyl)-amide

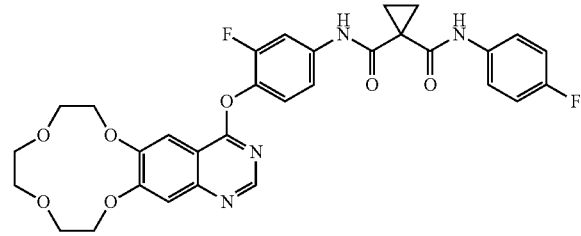 [SMILES: O=C(Nc1ccc(F)cc1)C1(C(=O)Nc2ccc(Oc3ncnc4cc5c(cc34)OCCOCCOCCO5)c(F)c2)CC1]

The desired title compound is synthesized by using the same sequence and conditions as described for Example 1 and 1-(4-Fluoro-phenylcarbamoyl)-cyclopropanecarboxylic acid (J. Med. Chem. 2008, 51, 5330-5341) used instead of 5-(4-Fluorophenyl)-4-oxo-1,4-dihydro-pyridine-3-carboxylic acid. ¹HNMR (400 MHz, DMSO) δ 10.33 (s, 1H), 10.08 (s, 1H), 8.56 (m, 1H), 7.82 (m, 2H), 7.69 (m, 2H), 7.28-7.51 (m, 3H), 7.19 (m, 2H), 4.35 (s, 4H), 3.87 (d, 4H), 3.62 (s, 4H), 1.47 (s, 4H). LC/MS Calcd for (M+H)⁺607.6. found 607.7.

Example 4

3-(4-Fluoro-phenyl)-2-oxo-imidazolidine-1-carboxylic acid [3-fluoro-4-(7,8,10,11,13,14-hexahydro-6,9,12,15-tetraoxa-1,3-diaza-cyclododeca[b]naphthalen-4-yloxy)-phenyl]-amide

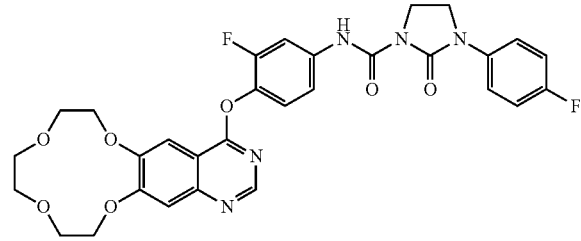 [SMILES: O=C(Nc1ccc(Oc2ncnc3cc4c(cc23)OCCOCCOCCO4)c(F)c1)N1CCN(c2ccc(F)cc2)C1=O]

The desired title compound is synthesized by using the same sequence and conditions as described for Example 1 and 3-(4-Fluoro-phenyl)-2-oxo-imidazolidine-1-carboxylic acid (J. Med. Chem. 2008, 51, 5330-5341) used instead of 5-(4-Fluorophenyl)-4-oxo-1,4-dihydro-pyridine-3-carboxylic acid. LC/MS Calcd for (M+H)⁺608.6. found 608.8.

Example 5

2-(4-Fluoro-phenyl)-1,5-dimethyl-3-oxo-2,3-dihydro-1H-pyrazole-4-carboxylic acid[3-fluoro-4-(7,8,10,11,13,14-hexahydro-6,9,12,15-tetraoxa-1,3-diaza-cyclododeca[b]naphthalen-4-yloxy)-phenyl]-amide

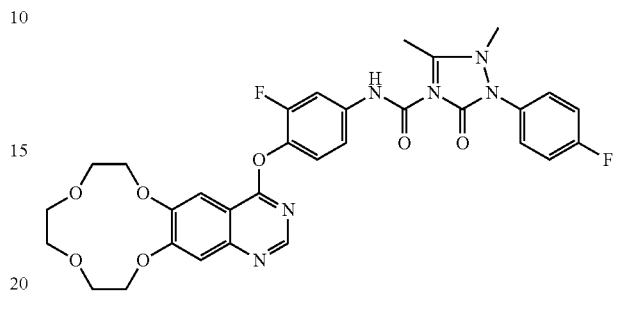

The desired title compound is synthesized by using the same sequence and conditions as described for Example 1 and 2-(4-Fluoro-phenyl)-1,5-dimethyl-3-oxo-2,3-dihydro-1H-pyrazole-4-carboxylic acid (J. Med. Chem. 2008, 51, 5330-5341) used instead of 5-(4-Fluorophenyl)-4-oxo-1,4-dihydro-pyridine-3-carboxylic acid. ¹HNMR (400 MHz, DMSO) δ 10.93 (s, 1H), 8.59 (s, 1H), 7.96 (d, 1H), 7.82 (s, 1H), 7.69 (m, 2H), 7.28-7.51 (m, 4H), 7.19 (m, 1H), 4.35 (s, 4H), 3.87 (d, 4H), 3.62 (s, 4H), 3.47 (s, 3H), 2.71 (s, 3H). LC/MS Calcd for (M+H)⁺634.6. found 634.8.

Example 6

2-(4-Fluoro-phenylamino)-5-[5-(7,8,10,11,13,14-hexahydro-6,9,12,15-tetraoxa-1,3-diaza-cyclododeca[b]naphthalen-4-yloxy)-pyridin-2-yl]-3-methyl-3H-pyrimidin-4-one

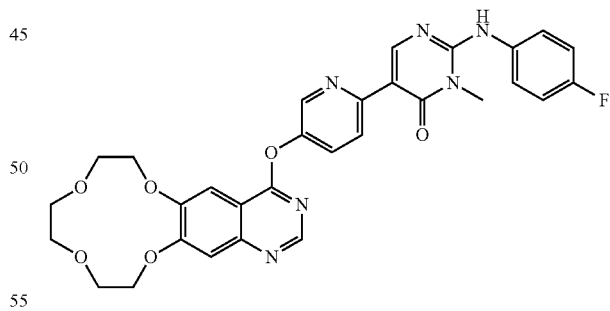

2-(4-Fluoro-phenylamino)-5-(5-hydroxy-pyridin-2-yl)-3-methyl-3H-pyrimidin-4-one (2.18 g, 7 mmol) was dissolved in dry DMF (30 ml) to which was added 60% NaH (774 mg, 19.3 mmol). After the mixture was stirred at room temperature for several minutes, a suspension of 4-Chloro-7,8,10,11,13,14-hexahydro-6,9,12,15-tetraoxa-1,3-diaza-cyclododeca[b]-naphthalene (2.08 g, 6.7 mmol) in dry DMF (40 ml) was added. The reaction mixture was stirred at room temperature for 1-2 hrs, then diluted with EtOAc and washed with sat'd NaHCO₃ (3×), H₂O (1×), sat'd NaCl (1×), dried (Na₂SO₄), and concentrated in vacuo to give crude title compound and further purification to yield product (3.68 g, 90%). ¹HNMR (400 MHz, DMSO): 9.18 (s, 1H), 8.60 (m, 3H), 8.45 (d, 1H), 7.84 (s, 1H), 7.82 (m, 1H), 7.55 (m, 3H), 7.21 (m, 2H), 4.35 (s, 4H), 3.87 (d, 4H), 3.62 (s, 4H). LC/MS Calcd for (M+H)⁺ 587.6. found 587.9.

Example 7

5-[5-([1,3]Dioxolo[4,5-g]quinazolin-8-yloxy)-pyridin-2-yl]-2-(4-fluoro-phenylamino)-3-methyl-3H-pyrimidin-4-one

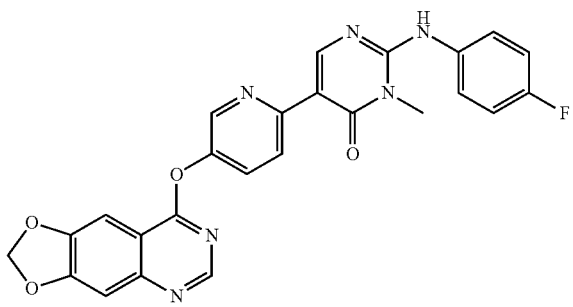 [SMILES: Cn1c(Nc2ccc(F)cc2)ncc(-c2ccc(Oc3ncnc4cc5c(cc34)OCO5)cn2)c1=O]

2-(4-Fluoro-phenylamino)-5-(5-hydroxy-pyridin-2-yl)-3-methyl-3H-pyrimidin-4-one (2.18 g, 7 mmol) was dissolved in dry DMF (30 ml) to which was added 60% NaH (774 mg, 19.3 mmol). After the mixture was stirred at room temperature for several minutes, a suspension of 8-Chloro-[1,3]dioxolo[4,5-g]quinazoline (2.08 g, 6.7 mmol) in dry DMF (40 ml) was added. The reaction mixture was stirred at room temperature for 1-2 hrs, then diluted with EtOAc and washed with sat'd NaHCO₃ (3×), H₂O (1×), sat'd NaCl (1×), dried (Na₂SO₄), and concentrated in vacuo to give crude title compound and further purification to yield product (3.68 g, 90%). ¹HNMR (400 MHz, DMSO): 9.18 (s, 1H), 8.60 (m, 3H), 8.45 (d, 1H), 7.84 (s, 1H), 7.82 (m, 1H), 7.55 (m, 3H), 7.21 (m, 2H), 4.15 (s, 2H). LC/MS Calcd for (M+H)⁺485.4. found 485.9.

Example 8

5-[5-(2,2-Difluoro-[1,3]dioxolo[4,5-g]quinazolin-8-yloxy)-pyridin-2-yl]-2-(4-fluoro-phenylamino)-3-methyl-3H-pyrimidin-4-one

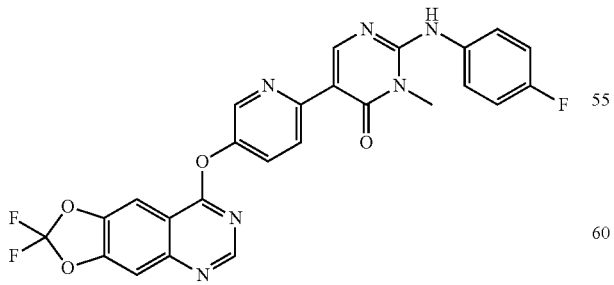

2-(4-Fluoro-phenylamino)-5-(5-hydroxy-pyridin-2-yl)-3-methyl-3H-pyrimidin-4-one (2.18 g, 7 mmol) was dissolved in dry DMF (30 ml) to which was added 60% NaH (774 mg, 19.3 mmol). After the mixture was stirred at room temperature for several minutes, a suspension of 4-Chloro-7,8,10,11,13,14-hexahydro-6,9,12,15-tetraoxa-1,3-diaza-cyclododeca[b]naphthalene (2.08 g, 6.7 mmol) in dry DMF (40 ml) was added. The reaction mixture was stirred at room temperature for 1-2 hrs, then diluted with EtOAc and washed with sat'd NaHCO₃ (3×), H₂O (1×), sat'd NaCl (1×), dried (Na₂SO₄), and concentrated in vacuo to give crude title compound and further purification to yield product (3.68 g, 90%). ¹HNMR (400 MHz, DMSO): 9.18 (s, 1H), 8.70 (m, 3H), 8.55 (d, 1H), 7.84 (s, 1H), 7.82 (m, 1H), 7.55 (m, 3H), 7.21 (m, 2H). LC/MS Calcd for (M+H)⁺521.4. found 521.6.

Example 9

5-(4-Fluoro-phenyl)-4-oxo-1,4-dihydro-pyridine-3-carboxylic acid [4-([1,3]dioxolo[4,5-g]quinazolin-8-yloxy)-3-fluoro-phenyl]-amide

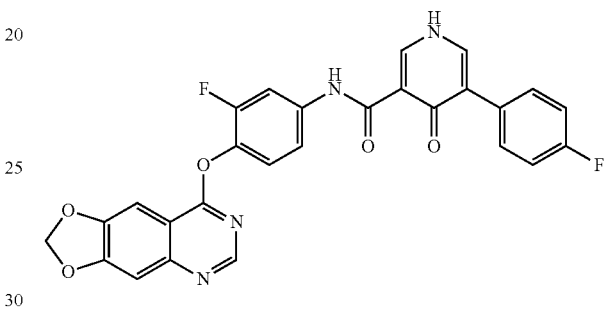

2-(4-Fluoro-phenylamino)-5-(5-hydroxy-pyridin-2-yl)-3-methyl-3H-pyrimidin-4-one (2.18 g, 7 mmol) was dissolved in dry DMF (30 ml) to which was added 60% NaH (774 mg, 19.3 mmol). After the mixture was stirred at room temperature for several minutes, a suspension of 4-Chloro-7,8,10,11,13,14-hexahydro-6,9,12,15-tetraoxa-1,3-diaza-cyclododeca[b]-naphthalene (2.08 g, 6.7 mmol) in dry DMF (40 ml) was added. The reaction mixture was stirred at room temperature for 1-2 hrs, then diluted with EtOAc and washed with sat'd NaHCO₃ (3×), H₂O (1×), sat'd NaCl (1×), dried (Na₂SO₄), and concentrated in vacuo to give crude title compound and further purification to yield product (3.68 g, 90%). ¹HNMR (400 MHz, DMSO) δ 13.43 (s, 1H), 12.98 (br s, 1H), 8.82 (m, 2H), 7.97-8.12 (m, 2H), 8.04-7.99 (m, 2H), 7.78 (m, 1H), 7.69 (m, 2H), 7.42 (d, 2H), 7.21 (m, 2H); 4.65 (s, 4H). LC/MS Calcd for (M+H)⁻515.4. found 515.5.

Example 10

5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1-aza-cyclododeca[b]naphthalen-4-yloxy)-phenyl]-amide

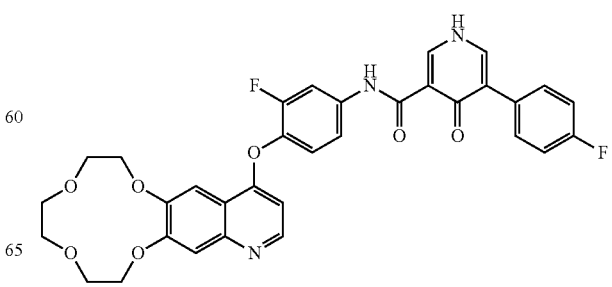

Step 1. 1-(3-Nitro-6,7,9,10,12,13-hexahydro-5,8,11,14-tetraoxa-benzocyclododecen-2-yl)-ethanone 1-(6,7,9,10,12,13-Hexahydro-5,8,11,14-tetraoxa-benzocyclododecen-2-yl)-ethanone (200 mmol, 51.3 g) dissolved in DCM (750 ml) and the mixture cooled to 0° C. Nitric acid (90%, 300 mmol, 14 ml) was added dropwise to the cooled solution over 20 minutes. Sulfuric acid (96.2%, 300 mmol, 8.75 ml) was then added dropwise over 40 minutes at 0° C. Additional nitric acid (200 mmol, 9.4 ml) was added dropwise over 20 minutes. The reaction mixture was diluted with water (300 ml) and wash with water (3×200 ml), Sat. NaHCO$_3$ (4×200 ml, or until neutral). The organic layer was dried over Na$_2$SO$_4$ and concentrated. The crude mixture was recrystallized with DMF to give 22.5 g of the nitro product. The DMF layer was concentrated and recrystallized with ethyl acetate to give additional 8.75 g of the product. The ethyl acetate layer was concentrated and purified on silica column using 20% EtOAc/hexanes to give another 4.75 g of the product. Total yield is 36 g, (~60%). $^1$HNMR (400 MHz, DMSO) δ 7.82 (s, 1H), 7.61 (s, 1H), 4.35 (s, 4H), 3.87 (d, 4H), 3.62 (s, 4H), 2.71 (s, 3H). LC/MS Calcd for (M+H)$^-$312.3. found 312.5.

Step 2. 1-(3-Amino-6,7,9,10,12,13-hexahydro-5,8,11,14-tetraoxa-benzocyclododecen-2-yl)-ethanone A Mixture of iron powder (477 mmol, 27 g), ammonium acetate (500 mmol, 31 g), 1-(3-Nitro-6,7,9,10,12,13-hexahydro-5,8,11,14-tetraoxa-benzocyclododecen-2-yl)-ethanone (120 mmol, 36 g), toluene (500 ml) and water (500 ml) was refluxed overnight, or until completion. The mixture was filtered through celite and washed with EtOAc. The organic layer was washed with water and Sat. NaCl, dried over Na$_2$SO$_4$, and concentrated to afford the product, 90%. $^1$HNMR (400 MHz, DMSO) δ 7.82 (s, 1H), 7.61 (s, 1H), 5.45 (s, 2H), 4.35 (s, 4H), 3.87 (d, 4H), 3.62 (s, 4H), 2.71 (s, 3H). LC/MS Calcd for (M+H)$^+$282.3. found 282.5.

Step 3. 7,8,10,11,13,14-Hexahydro-1H-6,9,12,15-tetraoxa-1-aza-cyclododeca[b]naphthalen-4-one To a solution of 1-(3-Amino-6,7,9,10,12,13-hexahydro-5,8,11,14-tetraoxa-benzocyclododecen-2-yl)-ethanone (108 mmol, 29.3 g) in DME (700 ml) was added sodium methoxide (432 mmol, 23.35 g). The mixture was stirred for 30 minutes. Ethyl formate (540 mmol, 44 ml) was added and the mixture was stirred overnight. (Additional sodium methoxide may be needed if reaction is not complete as monitored by LC/MS.) After the reaction was completion, the mixture was diluted with water (40 ml) and acidified to neutral with 1M HC 1. The precipitate was filtered and washed with water, dried in vacuo to afford 22 g (72%) of 7,8,10,11,13,14-Hexahydro-1H-6,9,12,15-tetraoxa-1-aza-cyclododeca[b]naphthalen-4-one. $^1$HNMR (400 MHz, DMSO) δ 8.58 (s, 1H), 7.52 (s, 1H), 7.22 (s, 1H), 7.12 (m, 1H), 4.35 (s, 4H), 3.87 (d, 4H), 3.62 (s, 4H). LC/MS Calcd for (M+H)$^+$292.3. found 292.5.

Step 4. 4-(2-Fluoro-4-nitro-phenoxy)-7,8,10,11,13,14-hexahydro-6,9,12,15-tetraoxa-1-aza-cyclododeca[b]naphthalene To a round bottom flask equipped with a magnetic stir bar was added 7,8,10,11,13,14-Hexahydro-1H-6,9,12,15-tetraoxa-1-aza-cyclododeca[b]naphthalen-4-one (12.2 g, 43.3 mmol, 1.0 eq.), acetonitrile (150 ml), DMF (150 ml) and cesium carbonate (28.2 g, 86.5 mmol, 2.0 eq). The mixture was stirred at room temperature for 30 minutes at which time 1,2-difluoro-4-nitro-benzene (7.57 g, 47.6 mmoL, 1.1 eq) was added over a 10 minute period. After 2 hours the reaction was complete at which time 75% of the MeCN and DMF were removed and the resulting solution was poured over into ice water. The solid was filtered and dried and further columned with a biotage system. The eluent was 1:3 ethyl acetate/hexane. Removal of the solvent afforded 4-(2-Fluoro-4-nitro-phenoxy)-7,8,10,11,13,14-hexahydro-6,9,12,15-tetraoxa-1-aza-cyclodo-deca[b]naphthalene as a pale green solid (7.4 g, 41% yield). $^1$HNMR (400 MHz, DMSO): 8.58 (s, 1H), 7.80 (s, 1H), 7.50 (s, 1H), 7.04 (t, 1H), 6.88 (m, 1H), 6.50 (m, 2H), 4.35 (s, 4H), 3.87 (d, 4H), 3.62 (s, 4H). LC/MS Calcd for (M+H)$^+$431.4. found 431.5.

Step 5. 4-(4-Amino-2-Fluoro-phenoxy)-7,8,10,11,13,14-hexahydro-6,9,12,15-tetraoxa-1-aza-cyclododeca[b]naphthalene To a par hydrogenation reaction vessel was 4-(2-Fluoro-4-nitro-phenoxy)-7,8,10,11,13,14-hexahydro-6,9,12,15-tetraoxa-1-aza-cyclododeca[b]naphthalene (0.800 g, 1.6 mmol, 1.0 eq.), DMF (50 ml), EtoAc (50 ml), MeOH (50 ml), TEA (5 ml) and 10% Pd/C (200 mg). The vessel was placed on the par hydrogenator at 35 psi overnight. The Pd was filtered and the solvent removed to give 4-(4-Amino-2-Fluoro-phenoxy)-7,8,10,11,13,14-hexahydro-6,9,12,15-tetraoxa-1-aza-cyclododeca[b]naphthalene as an off yellow solid (0.78 g, 99% yield). $^1$HNMR (400 MHz, DMSO): 8.58 (s, 1H), 7.80 (s, 1H), 7.50 (s, 1H), 7.04 (t, 1H), 6.88 (m, 1H), 6.50 (m, 2H), 5.40 (br s, 2H), 4.35 (s, 4H), 3.87 (d, 4H), 3.62 (s, 4H). LC/MS Calcd for (M+H)$^+$401.4. found 401.5.

Step 6. 5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1-aza-cyclododeca[b]naphthalen-4-yloxy)-phenyl]-amide To a suspension of 5-(4-Fluorophenyl)-4-oxo-1,4-dihydropyridine-3-carboxylic acid 8 d (J. Med. Chem. 2008, 51, 5330-5341) (8.0 g, 34.3 mmol) in anhydrous DMF (56 ml) were added HATU (15.65 g, 41.2 mmol) and i-Pr$_2$NEt (18 mL, 104 mmol) at ice bath temperature under nitrogen. The mixture turned into a clear solution after being stirred for 5 min. To the solution was added 4-(4-Amino-2-Fluoro-phenoxy)-7,8,10,11,13,14-hexahydro-6,9,12,15-tetraoxa-1-aza-cyclododeca[b]naphthalene 7a (7.9 g, 32.5 mmol) slowly. The reaction mixture was stirred for 3 h at room temperature and was poured into aqueous 1N HCl solution. The solid that formed was filtered, washed with distilled water, and dried. The crude product was purified by silica gel chromatography, eluting with 1-5% of MeOH in CH$_2$Cl$_2$ to obtain 9a as a light-yellow solid (5.9 g, 40%), mp 188-190° C. HPLC purity 97%; $^1$HNMR (400 MHz, DMSO) δ 13.13 (s, 1H), 12.68 (br s, 1H), 8.62 (m, 2H), 7.97-8.12 (m, 2H), 8.04-7.99 (m, 2H), 7.78 (m, 1H), 7.69 (m, 2H), 7.42 (d, 2H), 7.21 (m, 2H); 6.89 (m, 1H), 4.35 (s, 4H), 3.87 (d, 4H), 3.62 (s, 4H). LC/MS Calcd for (M+H)$^+$616.6. found 616.5.

Example 11

1-(4-Fluoro-phenyl)-2-oxo-1,2-dihydro-pyridine-3-carboxylic acid [3-fluoro-4-(7,8,10,11,13,14-hexahydro-6,9,12,15-tetraoxa-1-aza-cyclododeca[b]naphthalen-4-yloxy)-phenyl]-amide

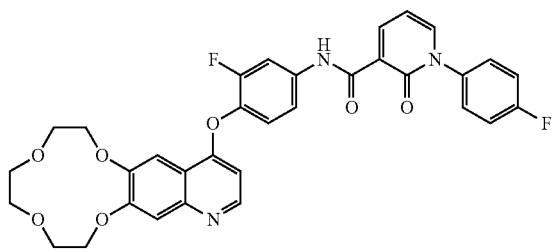 [SMILES: O=C(Nc1ccc(Oc2ccnc3cc4c(cc23)OCCOCCOCCO4)c(F)c1)c1cccn(-c2ccc(F)cc2)c1=O]

The desired title compound is synthesized by using the same sequence and conditions as described for Example 6 and 1-(4-Fluorophenyl)-2-oxo-1,2-dihydropyridine-3-carboxylic acid used instead of 5-(4-Fluorophenyl)-4-oxo-1,4-dihydro-pyridine-3-carboxylic acid. LC/MS Calcd for $(M+H)^+$ 616.6. found 616.5.

Example 12

2-(4-Fluoro-phenyl)-1,5-dimethyl-3-oxo-2,3-dihydro-1H-pyrazole-4-carboxylic acid [3-fluoro-4-(7,8,10,11,13,14-hexahydro-6,9,12,15-tetraoxa-1-aza-cyclododeca[b]naphthalen-4-yloxy)-phenyl]-amide

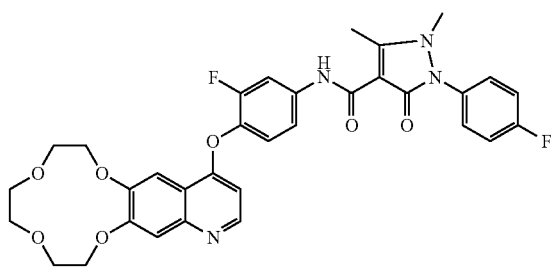 [SMILES: Cc1c(C(=O)Nc2ccc(Oc3ccnc4cc5c(cc34)OCCOCCOCCO5)c(F)c2)c(=O)n(-c2ccc(F)cc2)n1C]

The desired title compound is synthesized by using the same sequence and conditions as described for Example 6 and 2-(4-Fluoro-phenyl)-1,5-dimethyl-3-oxo-2,3-dihydro-1H-pyrazole-4-carboxylic acid used instead of 5-(4-Fluorophenyl)-4-oxo-1,4-dihydro-pyridine-3-carboxylic acid. $^1$HNMR (400 MHz, DMSO) δ 10.93 (s, 1H), 8.59 (s, 1H), 7.96 (d, 1H), 7.82 (s, 1H), 7.69 (m, 2H), 7.28-7.51 (m, 4H), 7.19 (m, 1H), 6.46 (m, 1H), 4.35 (s, 4H), 3.87 (d, 4H), 3.62 (s, 4H), 3.47 (s, 3H), 2.71 (s, 3H). LC/MS Calcd for $(M+H)^+$ 633.6. found 633.8.

Example 13

Cyclopropane-1,1-dicarboxylic acid[3-fluoro-4-(7,8,10,11,13,14-hexahydro-6,9,12,15-tetraoxa-1-aza-cyclododeca[b]naphthalen-4-yloxy)-phenyl]-amide (4-fluoro-phenyl)-amide

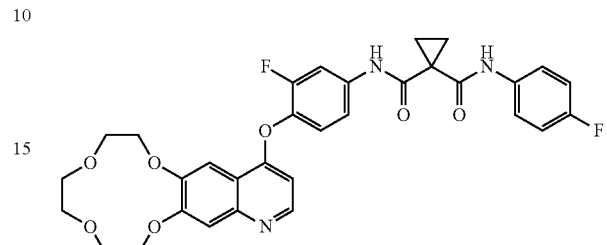

The desired title compound is synthesized by using the same sequence and conditions as described for Example 6 and 1-(4-Fluoro-phenylcarbamoyl)-cyclopropanecarboxylic acid used instead of 5-(4-Fluorophenyl)-4-oxo-1,4-dihydro-pyridine-3-carboxylic acid. $^1$HNMR (400 MHz, DMSO) δ 10.33 (s, 1H), 10.08 (s, 1H), 8.56 (m, 1H), 7.82 (m, 2H), 7.69 (m, 2H), 7.28-7.51 (m, 3H), 7.19 (m, 2H), 6.88 (m, 1H), 4.35 (s, 4H), 3.87 (d, 4H), 3.62 (s, 4H), 1.47 (s, 4H). LC/MS Calcd for $(M+H)^+$ 606.6. found 606.7.

Example 14

3-(4-Fluoro-phenyl)-2-oxo-imidazolidine-1-carboxylic acid [3-fluoro-4-(7,8,10,11,13,14-hexahydro-6,9,12,15-tetraoxa-1-aza-cyclododeca[b]naphthalen-4-yloxy)-phenyl]-amide

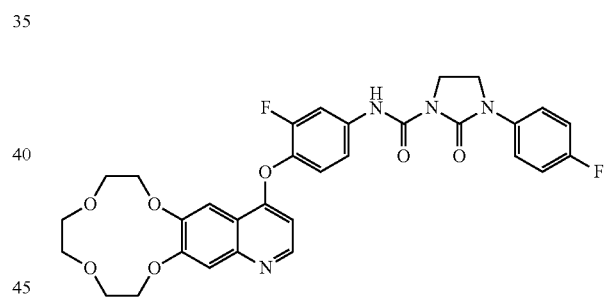

The desired title compound is synthesized by using the same sequence and conditions as described for Example 6 and 3-(4-Fluoro-phenyl)-2-oxo-imidazolidine-1-carboxylic acid used instead of 5-(4-Fluorophenyl)-4-oxo-1,4-dihydro-pyridine-3-carboxylic). LC/MS Calcd for $(M+1-1)^+$ 607.6. found 607.7.

| Ex No | Chemical Name | Structure | Physical Data (MS) $(M+H)^+$ |
|---|---|---|---|
| 15 | 5-[5-(2,2-Difluoro-[1,3]dioxolo[4,5-g]quinazolin-8-yloxy)-pyridin-2-yl]-2-(2-fluoro-phenylamino)-3-methyl-3H-pyrimidin-4-one | 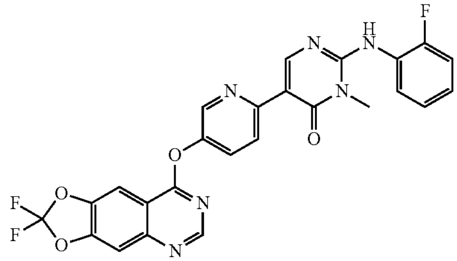 [SMILES: Cn1c(Nc2ccccc2F)ncc(-c2ccc(Oc3ncnc4cc5c(cc34)OC(F)(F)O5)cn2)c1=O] | 521.2 |

-continued

| Ex No | Chemical Name | Structure | Physical Data (MS) (M + H)+ |
|---|---|---|---|
| 16 | 5-[5-(2,2-Difluoro-[1,3]dioxolo[4,5-g]quinazolin-8-yloxy)-pyridin-2-yl]-2-(phenylamino)-3-methyl-3H-pyrimidin-4-one | 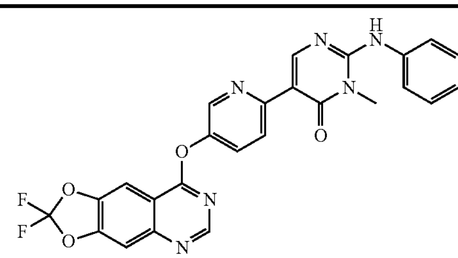 | 503.2 |
| 17 | 5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1-aza-cyclododeca[b]naphthalen-4-ylamino)-phenyl]-amide | 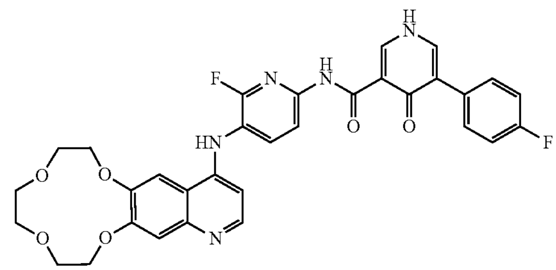 [SMILES: O=C(Nc1ccc(Nc2ccnc3cc4c(cc23)OCCOCCOCCO4)c(F)n1)c1c[nH]cc(-c2ccc(F)cc2)c1=O] | 615.6 |
| 18 | 5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1-aza-cyclododeca[b]naphthalen-4-ylsulfanyl)-phenyl]-amide | 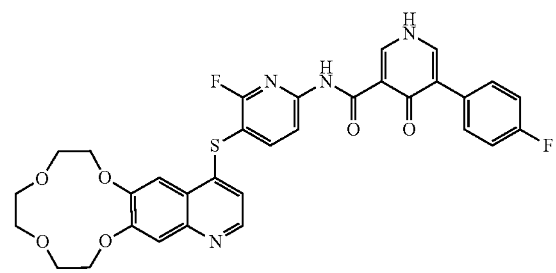 [SMILES: O=C(Nc1ccc(Sc2ccnc3cc4c(cc23)OCCOCCOCCO4)c(F)n1)c1c[nH]cc(-c2ccc(F)cc2)c1=O] | 632.9 |
| 19 | 3-Methyl-2-phenylamino-5-[5-(2,5,7,10-tetraoxa-14,16-diaza-tricyclo[9.8.0.0$^{13,18}$]nonadeca-1(11),12,14,16,18-pentaen-17-yloxy)-pyridin-2-yl]-3H-pyrimidin-4-one | 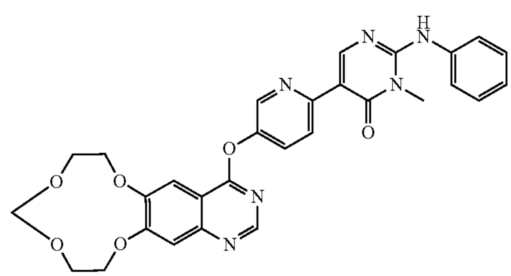 [SMILES: Cn1c(Nc2ccccc2)ncc(-c2ccc(Oc3ncnc4cc5c(cc34)OCCOCOCCO5)cn2)c1=O] | 555.8 |
| 20 | 5-[5-(8,9-Dihydro-7H-6,10-dioxa-1,3-diaza-cyclohepta[b]naphthalen-4-yloxy)-pyridin-2-yl]-2-(4-fluoro-phenylamino)-3-methyl-3H-pyrimidin-4-one | 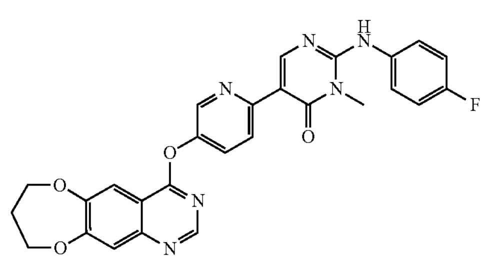 [SMILES: Cn1c(Nc2ccc(F)cc2)ncc(-c2ccc(Oc3ncnc4cc5c(cc34)OCCCO5)cn2)c1=O] | 513.6 |
| 21 | 2-(4-Fluoro-phenylamino)-3-methyl-5-[5-(9-methyl-8,9,10,11-tetrahydro-7H-6,12-dioxa-1,3,9-triaza-cyclonona[b]naphthalen-4-yloxy)-pyridin-2-yl]-3H-pyrimidin-4-one | 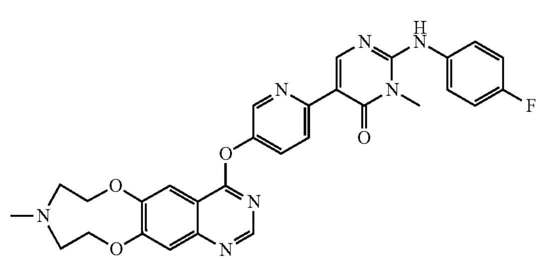 [SMILES: CN1CCOc2cc3ncnc(Oc4ccc(-c5cnc(Nc6ccc(F)cc6)n(C)c5=O)nc4)c3cc2OCC1] | 556.9 |

-continued

| Ex No | Chemical Name | Structure | Physical Data (MS) (M + H)+ |
|---|---|---|---|
| 22 | 2-(4-Fluoro-phenylamino)-3-methyl-5-[5-(7,8,10,11-tetrahydro-6,9,12-trioxa-1,3-diaza-cyclonona[b]naphthalen-4-yloxy)-pyridin-2-yl]-3H-pyrimidin-4-one | 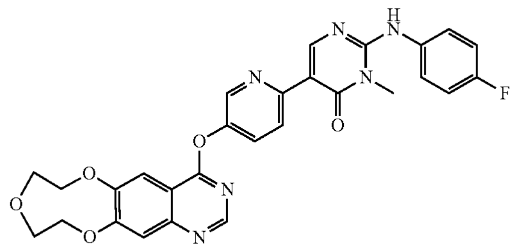 [SMILES: Cn1c(Nc2ccc(F)cc2)ncc(-c2ccc(Oc3ncnc4cc5c(cc34)OCCOCCO5)cn2)c1=O] | 543.6 |
| 23 | 5-[5-(8,9-Dihydro-7H-6,10-dioxa-1-aza-cyclohepta[b]naphthalen-4-yloxy)-pyridin-2-yl]-2-(4-fluoro-phenylamino)-3-methyl-3H-pyrimidin-4-one | 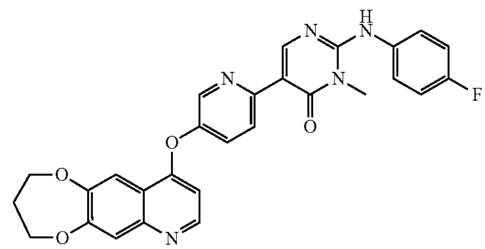 [SMILES: Cn1c(Nc2ccc(F)cc2)ncc(-c2ccc(Oc3ccnc4cc5c(cc34)OCCCO5)cn2)c1=O] | 512.6 |
| 24 | 2-(4-Fluoro-phenylamino)-3-methyl-5-[5-(9-methyl-8,9,10,11-tetrahydro-7H-6,12-dioxa-1,9-diaza-cyclonona[b]naphthalen-4-yloxy)-pyridin-2-yl]-3H-pyrimidin-4-one | 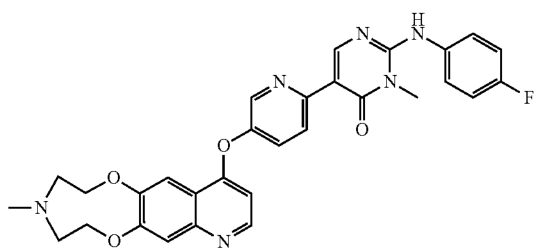 [SMILES: CN1CCOc2cc3nccc(Oc4ccc(-c5cnc(Nc6ccc(F)cc6)n(C)c5=O)nc4)c3cc2OCC1] | 555.6 |
| 25 | 2-(4-Fluoro-phenylamino)-3-methyl-5-[5-(7,8,10,11-tetrahydro-6,9,12-trioxa-1-aza-cyclonona[b]naphthalen-4-yloxy)-pyridin-2-yl]-3H-pyrimidin-4-one ne | 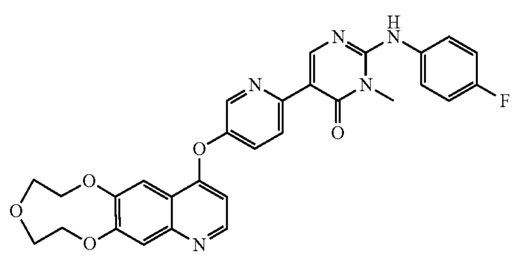 [SMILES: Cn1c(Nc2ccc(F)cc2)ncc(-c2ccc(Oc3ccnc4cc5c(cc34)OCCOCCO5)cn2)c1=O] | 542.3 |
| 26 | 3-Methyl-2-phenylamino-5-[5-(2,5,7,10-tetraoxa-14-aza-tricyclo[9.8.0.013,18]nonadeca-1(11),12,14,16,18-pentaen-17-yloxy)-pyridin-2-yl]-3H-pyrimidin-4-one | 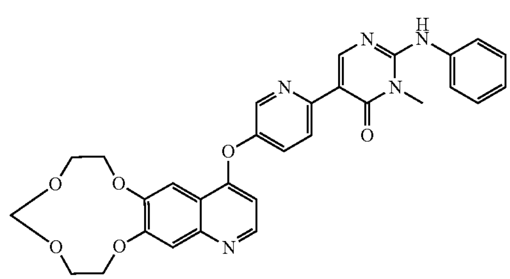 [SMILES: Cn1c(Nc2ccccc2)ncc(-c2ccc(Oc3ccnc4cc5c(cc34)OCCOCOCCO5)cn2)c1=O] | 554.3 |
| 27 | 5-[5-(2,2-Difluoro-[1,3]dioxolo[4,5-g]quinolin-8-yloxy)-pyridin-2-yl]-2-(2-fluoro-phenylamino)-3-methyl-3H-pyrimidin-4-one | 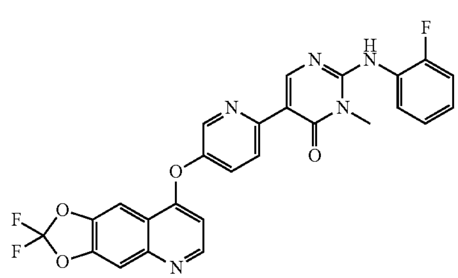 [SMILES: Cn1c(Nc2ccccc2F)ncc(-c2ccc(Oc3ccnc4cc5c(cc34)OC(F)(F)O5)cn2)c1=O] | 520.3 |

-continued

| Ex No | Chemical Name | Structure | Physical Data (MS) (M + H)+ |
|---|---|---|---|
| 28 | 5-[5-(2,2-Difluoro-[1,3]dioxolo[4,5-g]quinolin-8-yloxy)-pyridin-2-yl]-2-(phenylamino)-3-methyl-3H-pyrimidin-4-one | 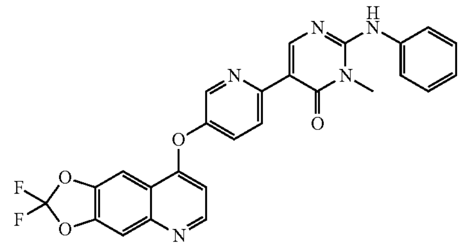 [SMILES: Cn1c(Nc2ccccc2)ncc(-c2ccc(Oc3ccnc4cc5c(cc34)OC(F)(F)O5)cn2)c1=O] | 502.4 |
| 29 | 5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1,3-diaza-cyclododeca[b]naphthalen-4-ylamino)-phenyl]-amide | 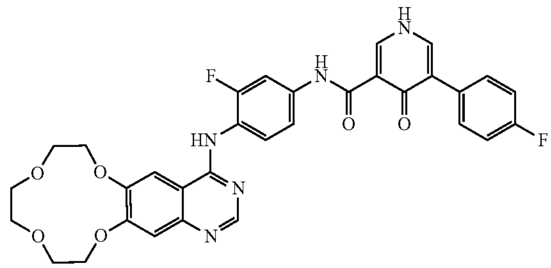 [SMILES: O=C(Nc1ccc(Nc2ncnc3cc4c(cc23)OCCOCCOCCO4)c(F)c1)c1c[nH]cc(-c2ccc(F)cc2)c1=O] | 616.6 |
| 30 | 5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1,3-diaza-cyclo dodeca[b]naphthalen-4-ylsulfanyl)-phenyl]-amide | 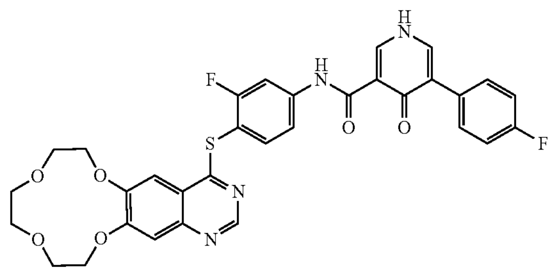 [SMILES: O=C(Nc1ccc(Sc2ncnc3cc4c(cc23)OCCOCCOCCO4)c(F)c1)c1c[nH]cc(-c2ccc(F)cc2)c1=O] | 633.7 |
| 31 | 5-[5-(2,5,8,11,14,17-Hexaoxa-21-aza-tricyclo[16.8.0.020,25]hexacosa-1(18), 19,21,23,25-pentaen-24-yloxy)-pyridin-2-yl]-3-methyl-2-phenylamino-3 H-pyrimidin-4-one | 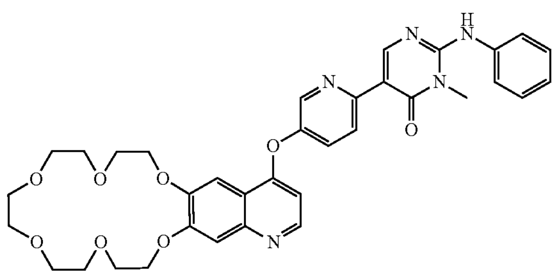 [SMILES: Cn1c(Nc2ccccc2)ncc(-c2ccc(Oc3ccnc4cc5c(cc34)OCCOCCOCCOCCOCCO5)cn2)c1=O] | 656.7 |

Pharmacological Testing

The following assays demonstrate that certain compounds of the present invention potently inhibit c-Met phosphorylation in cells, potently inhibit c-Met in vivo, and demonstrate dose dependent anti-tumor activity in certain xenograft models.

Biological Assays

The kinase domain (KD) of human c-Met (from Gly 966 to Ser 1390, NCBI NM_000245) is cloned into a pFastBac®HT vector (Invitrogen, Carlsbad, Calif.). The His-c-Met KD construct is transposed into Baculovirus DNA using a Bac-to-Bac® system (Invitrogen). SF9 cells are infected with the recombinant baculovirus. The infected cells are harvested by centrifugation and the cell pellet is collected and stored at −80° C. Cells are lysed in buffer A (40 mM tris(hydroxymethyl)aminomethane (Tris), pH7.5, 500 mM NaCl, 20% glycerol, and 10 mM imidazole). Cell lysates are homogenized and centrifuged. Supernatants are incubated with nickel-nitrilotriacetic (Ni-NTA) resin and loaded onto a column. Proteins are eluted with buffer B (buffer A plus 0.3M imidazole) and c-Met containing fractions are pooled together, loaded onto a Superdex®200 column (Amershan Bioscience, Piscataway, N.J.), eluted with buffer C (40 mM Tris, pH7.5, 250 mM NaCl, and 10% glycerol).

HGF Stimulated Met (pY1349) NCI-H460 Cell-based ELISA NCI-H460 cells (purchased from ATCC) are cultured in RPMI 1640 media (Invitrogen) supplemented with 10% Fetal Bovine Serum (FBS) and plated (prior to becoming 70% confluent) in 96-well flat-bottom plates at a density of 20,000 cells per well in 80 μL volume. The cells are then incubated overnight in a cell culture incubator (5% $CO_2$, 95% Relative Humidity (RH) and 37° C.) and allowed to attach to the plate. The following morning the cells are washed with 2 volumes of a Reduced Serum Media (RSM) (RPMI 1640 media supplemented with 0.5% FBS). After removal of the last wash, 804 of RSM is added to each well of the cell plates. The cell plates are incubated for 2.5 hours in a cell culture incubator, and then dosed with compounds. Compound inhibitors are first solubilized at 10 mM in 100% DMSO and then diluted to 100 µM with 2% DMSO RSM. Subsequently compound serial dilutions (1:3) are prepared over a 100 µM to 0.005 µM range. Cells are dosed with the addition of 20 µL of compound stock to produce a final DMSO concentration of 0.4% and a final compound concentration dose range between 20 and 0.001 µM. After dosing with compounds the cells plates are gently agitated to mix and then allowed to incubate for 30 min in a cell culture incubator. After dose completion, the cells are stimulated with the addition of 20 µL per well of Hepatocyte Growth Factor (HGF) at a final concentration of 100 ng/mL in RSM (all wells except MIN wells are stimulated, MIN wells are dosed with 20 µL RSM). After 10 min incubation in a cell culture incubator, the liquid is removed from the cell plate wells, and the cells are lysed by the addition of 50 µL of ice-cold Meso Scale Discovery® (MSD, Gaithersburg, Md.) IX Lysis Buffer (150 mM NaCl, 20 mM Tris, pH7.5, 1 mM EDTA, 1 mM ethylene glycol tetraacetic acid, and 1% TRITON® X-100) supplemented with Phosphatase I and II and Protease inhibitors (Sigma, St. Louis, Mo.). After lysis at RT for 30 min the lysates are transferred to and captured on a MSD® Multi-Spot 96-well.

TABLE 1

| Example | Counts | Mean (Counts − Blanks) | Activity (% Control) | Mean | SD* |
|---|---|---|---|---|---|
| 6 - 0.2 µM | 30847 | 29068 | 29 | 25 | 5 |
|  | 29093 |  | 21 |  |  |
| 8 - 0.2 µM | 30429 | 28728 | 27 | 24 | 5 |
|  | 28830 |  | 20 |  |  |
| 9 - 0.2 µM | 28364 | 27649 | 18 | 19 | 1 |
|  | 28738 |  | 20 |  |  |
| 10 - 0.2 µM | 30524 | 28866 | 28 | 25 | 5 |
|  | 29012 |  | 21 |  |  |
| 11 - 0.2 µM | 32582 | 31407 | 36 | 35 | 2 |
|  | 32035 |  | 34 |  |  |
| 20 - 0.2 µM | 34234 | 32073 | 44 | 39 | 8 |
|  | 31716 |  | 33 |  |  |
| 21 - 0.2 µM | 31741 | 29384 | 33 | 27 | 9 |
|  | 28830 |  | 20 |  |  |
| 1 - 0.2 µM | 1008 | 50 | 0 | 0 | 0 |
|  | 895 |  | 0 |  |  |
| 31 - 0.2 µM | 20248 | 17936 | 43 | 37 | 9 |
|  | 17427 |  | 31 |  |  |
| 28 - 0.2 µM | 1070 | 30 | 1 | 1 | 1 |
|  | 793 |  | 0 |  |  |
| CONTROL | 23448 | 23217 | 97 | 100 | 3 |
|  | 23600 |  | 98 |  |  |
|  | 24600 |  | 102 |  |  |
|  | 24829 |  | 103 |  |  |
| BLANK | 982 | / | / | / | / |
|  | 822 |  | / |  |  |

4-spot PhosphoMet plate that is BSA-blocked (at 30 mg/mL Block A in IX Tris Wash Buffer) and then washed one time with Tris Wash Buffer. After 2 hours capture (at RT) the lysates are removed from the MSD® plate and the plate is washed with IX Tris Wash Buffer. After blotting, 25 µL of 5 nM Sulfo-Tag Anti-Total Met antibody (detection antibody, MSD®) prepared in IX Tris Wash Buffer supplemented with 10 mg/mL BSA and 0.1% Blocker D-R (MSD®)) is added to the wells of the MSD® plate. After 1 hour capture (at RT) the MSD® plate wells are washed with IX Tris Wash Buffer, and then 150 µL of IX Read Buffer T (with surfactant, MSD®) is added. Immediately after the addition of the Read Buffer, the plates are analyzed with a SECTOR 6000 MSD® Imager plate reader. Relative IC50 values are determined using MSD activity units by calculating percent inhibition with respect to on-plate "MIN" and "MAX" controls and then fitting the percent inhibition values and ten-point dose response data to a four-parameter logistic equation. This assay has a Minimum Significant Ratio (MSR) of 2.06. For all exemplified compounds the IC50 values are less than 0.2 µM (Table1). For example, the average (n=6) IC50 value (50% inhibitory concentration) of Example 1 in this assay is 0.0352 µM, indicating it potently inhibits c-Met phosphorylation in cells.

c-Met In Vivo Target Inhibition Assay

SI 14 cells (licensed from PHS, over-express both human HGF and human c-Met) are cultured in a growth media (Dulbecco's Modified Eagle Medium) supplemented with 10% fetal calf serum and expanded. Cells are harvested and washed twice with phosphate buffered saline and $2 \times 10^6$ cells are mixed with equal volume of BD Matrigel™ matrix (BD Bioscience, Franklin, N.J.), and injected subcutaneous ly into the flank of nude mice (athymic nude, from Harlan, Indianapolis, Ind.). At day 8 after implant, compounds (formulated in 10% acacia or 1% carboxymethylcellulose/0.5% sodium lauryl sulfate/0.05% antifoam as suspension) are administered to animals by oral gavage at 50 mg/kg. Animals are sacrificed at 2 hours post dose, and tumors are harvested and stored frozen until needed.

Frozen tumors are pulverized using motar-pastel. The pulverized tissues are transferred to a tube containing Lysing Matrix D beads (MP Biomedicals, Solon, Ohio) and 600 µL lysis buffer (RIPA buffer, containing 50 mM Tris-HCl, pH7.4, 150 mM NaCl, 1% NP-40, 0.5% sodium deoxycholate, 0.1% SDS, from Boston Bioproducts). A FastPrep® Cell Disrupter (MP Biomedicals) is used to disrupt the tissue and lyse the cells. Lysates are passed through a 20 gauge needle and transferred to a clean tube. Protein concentration is determined by Bradford method. Tumor lysates are loaded onto MSD® phosphor-Met ELISA plates and phosphor-c-Met level is determined using the same protocol as H460 cell-based ELISA. For all exemplified compounds the SI 14 in vivo inhibition values are equal or greater than 50% at the dose of 50 mg/kg. For example, Example 1 is a potent inhibitor of c-Met phosphorylation with an $ED_{50}$ value (dose that produces 50% inhibition in tumor of 2.9 mg/kg, indicating it is a potent c-Met inhibitor in vivo.

Xenograft Tumor Models

Human glioblastoma cells U87MG, human gastric cancer cells MKN45, human non small cell lung cancer cells H441, and human renal carcinoma cells Caki-1 are expanded in culture, harvested, and injected subcutaneous ly onto the rear flank of athymic nude mice. Testing compound is prepared in an appropriate vehicle and is administered by oral gavage when tumors are established (7-21 days after implant). Tumor response is determined by tumor volume measurement performed twice a week during the course of treatment. Tumor volume inhibition (% growth inhibition) is calculated by comparing treated groups to a vehicle control group. Body weight is taken as a general measurement of toxicity. The Compound of Example 1 demonstrates excellent dose dependent anti-tumor activity in these models. For example, when dosed at 30 mg/kg (oral (PO), bi-daily (BID)×35), Example 1 is able to cause 59% growth inhibition of U87MG tumors. At 60 mg/kg dose (PO, BID×35), 82% growth inhibition is achieved. At 120 mg/kg dose (PO, BID×35), 92% growth inhibition reaches.

c-Met relevant tumors and xenograft models c-Met overexpression is a common feature for many human tumors, including lung, breast, colorectal, gastric, renal, pancreatic, head and neck (1,2). c-Met activating mutations in the kinase domain are implicated as the cause for several tumors, such as hereditary papillary renal cell carcinoma, childhood hepatocellular carcinoma, and gastric cancer (3-7). c-Met inhibitors from Pfizer demonstrated antitumor efficacy in many human xenograft tumors, including U87MG, GTL16, H441, Caki-1, and PC3 (8).

1. Christinsen, J G, Burrows, J., and Salgia, R. Cancer Letters 225: 1-26, 2005.
2. Birchmeier, C, Birchmeier, W., Gherardi, E., and Vande Woude, G F. Nat Rev Mol Cell Biol 4: 915-925, 2003.
3. Di Renzo, M F., Olivero, M., Martone, T. Et al. Oncogene 19: 1547-1555, 2000.
4. Lee, J H., Han, S U, Cho, H. et al. Oncogene 19: 4947-4953, 2000.
5. Ma, P C, Kijima, T., Maulik, G et al. Cancer Res 63: 6272-6281, 2003.
6. Park, W S., Dong, S M., Kim, S Y. et al. Cancer Res 59: 307-310, 1999.
7. Schmidt, L., Duh, F M., Chen, F., et al. Nat Genet 16: 68-73, 1997.
8. Zou, H Y., Li, Qiuhua., Lee, J H., et al. Cancer Res 67: 4408-4417, 2007.

The compounds of the present invention are preferably formulated as pharmaceutical compositions administered by a variety of routes. Most preferably, such compositions are for oral administration. Such pharmaceutical compositions and processes for preparing the same are well known in the art. See, e.g., REMINGTON: THE SCIENCE AND PRACTICE OF PHARMACY (A. Gennaro, et al, eds., 19$^{th}$ ed., Mack Publishing Co., 1995). The compounds of Formula I are generally effective over a wide dosage range.

For example, dosages per day normally fall within the range of about 1 mg to about 200 mg total daily dose, preferably 1 mg to 150 mg total daily dose, more preferably 1 mg to 50 mg total daily dose. In some instances dosage levels below the lower limit of the aforesaid range may be more than adequate, while in other cases still larger doses may be employed. The above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

What is claimed is:
1. A compound according to Formula I

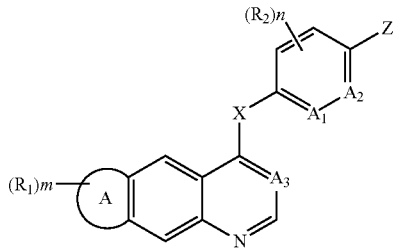

Formula I or a pharmaceutically acceptable salt thereof, wherein:

is a monocyclic 5-18 membered heterocyclyl, represented by the following formula:

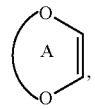

wherein Ring A contains 1-14 additional atoms independently selected from the group consisting of carbon, oxygen and nitrogen;

$R_1$ is halogen, $C_{1-8}$alkyl, $C_{2-8}$alkenyl, $C_{2-8}$alkynyl, aryl, heteroaryl, heterocyclyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alkynyloxy, $C_{1-8}$alkylthio, N—($C_{1-8}$alkyl)carbamoyl, N,N-di($C_{1-8}$alkyl)carbamoyl, $C_{1-8}$alkanoyloxy, $C_{1-8}$alkanoylamino, $C_{3-8}$alkynoylamino, N—($C_{1-8}$alkyl)sulfamoyl, or N,N-di($C_{1-8}$alkyl) sulfamoyl;

m is 0, 1, 2, or 3;

$A_1$ and $A_2$ are each independently =N— or =C($R_2$)—;

$R_2$ is halogen, hydrogen, trihalomethyl, —CN, —NO$_2$, OR$_5$, —NR$_5$R$_6$, —S(O)$_{0-2}$R$_5$, —SO$_2$NR$_5$R$_6$, —CO$_2$R$_5$, —C(O)NR$_5$R$_6$, —N(R$_3$)SO$_2$R$_5$, —N(R$_5$)C(O)R$_6$, —N(R$_5$)CO$_2$R$_6$, —C(O)R$_5$, or lower alkyl; wherein $R_5$ and $R_6$ are each independently hydrogen, $C_{1-8}$alkyl, $C_{2-8}$alkenyl, $C_{2-8}$alkynyl, aryl, heteroaryl, heterocyclyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alkynyloxy, $C_{1-8}$alkylthio, N—($C_{1-8}$alkyl)carbamoyl, N,N-di($C_{1-8}$alkyl) carbamoyl, $C_{1-8}$alkanoyloxy, $C_{1-8}$alkanoylamino, $C_{3-8}$alkynoylamino, N—($C_{1-8}$alkyl) sulfamoyl, N,N-di $C_{1-8}$alkyl)sulfamoyl, $C_{1-8}$alkylaryl, $C_{1-8}$alkylheteroaryl, or $C_{1-8}$alkylheterocyclyl;

n is 0, 1, 2, 3, or 4;

$A_3$ is =N—, =C(H)—, or =C(CN)—;

X is NR$_{20}$, CHR$_{21}$, O, or S; wherein R$_{20}$ and R$_{21}$ are each independently H or $C_{1-8}$alkyl;

Z is —NR$_3$R$_4$ or Formula II, wherein

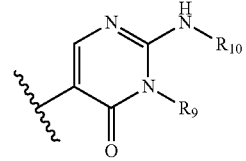

Formula II $R_9$ and $R_{10}$ are each independently $C_{1-8}$alkyl, $C_{2-8}$alkenyl, $C_{2-8}$alkynyl, aryl optionally substituted with halogen, heteroaryl optionally substituted with halogen, heterocyclyl, $C_{1-8}$alkanoyl, $C_{1-8}$alkoxycarbonyl, $C_{1-8}$alkylsulfinyl, $C_{1-8}$alkylsulfonyl, or arylsulfonyl;

$R_3$ is hydrogen, $C_{1-8}$alkyl, $C_{2-8}$alkenyl, $C_{2-8}$alkynyl, $C_{1-8}$alkanoyl, $C_{1-8}$alkoxycarbonyl, $C_{1-8}$alkylsulfinyl, $C_{1-8}$alkylsulfonyl, arylsulfonyl, cyano, nitro, hydroxy, amino, carboxy, oxo, carbamoyl, $C_{1-8}$alkoxy, $C_{2-8}$alkenyloxy, $C_{2-8}$alkynyloxy, $C_{1-8}$alkylthio, N—($C_{1-8}$alkyl) carbamoyl, N,N-di($C_{1-8}$alkyl)carbamoyl, $C_{1-8}$alkanoyloxy, $C_{1-8}$alkanoylamino, $C_{3-8}$alkynoylamino, N—($C_{1-8}$alkylsulfamoyl, or N,N-di($C_{1-8}$alkylsulfamoyl;

$R_4$ is Formula III, Formula IV, Formula V, Formula VI, or Formula VII:

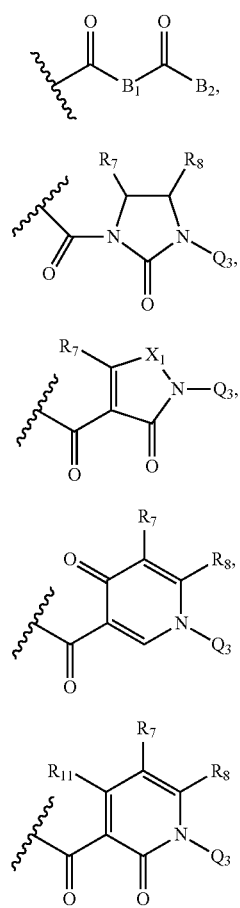

Formula III

Formula IV

Formula V

Formula VI

Formula VII wherein, $B_1$ is

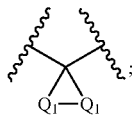

$Q_1$ is $C(R_5)_2$;

$B_2$ is $NHQ_2$;

$Q_2$ is aryl optionally substituted with halogen, heteroaryl optionally substituted with halogen, heterocyclyl, $C_{1-8}$alkylaryl, $C_{1-8}$alkylheteroaryl, or $C_{1-8}$alkylheterocyclyl;

or, $B_1$ and $B_2$, together with the —C(O)— group to which they are bonded, form a 5 to 10 member heteroaryl, or heterocyclyl;

$Q_3$ is hydrogen, aryl optionally substituted with halogen, heteroaryl optionally substituted with halogen, heterocyclyl, $C_{1-8}$alkylaryl, $C_{1-8}$alkylheteroaryl, or $C_{1-8}$alkylheterocyclyl;

$X_1$ is $NR_8$ or $CR_7R_8$;

and $R_7$, $R_8$ and $R_{11}$ are each independently hydrogen, halogen, $C_{1-8}$alkyl, $C_{2-8}$alkenyl, $C_{2-8}$alkynyl, aryl optionally substituted with halogen, heteroaryl optionally substituted with halogen, heterocyclyl, $C_{1-8}$alkanoyl, $C_{1-8}$alkoxycarbonyl, $C_{1-8}$alkylsulfinyl, $C_{1-8}$alkylsulfonyl, N—($C_{1-8}$alkyl)carbamoyl, N,N-di($C_{1-8}$alkyl)carbamoyl, $C_{1-8}$alkanoyloxy, arylsulfonyl, cyano, nitro, hydroxy, amino, carboxy, oxo, carbamoyl, $C_{1-8}$alkoxy, $C_{2-8}$alkenyloxy, $C_{2-8}$alkynyloxy, $C_{1-8}$alkylthio, $C_{1-8}$alkanoylamino, $C_{3-8}$alkynoylamino, N—($C_{1-8}$alkyl)sulfamoyl, N,N-di($C_{1-8}$alkyl)sulfamoyl, $C_{1-8}$alkylaryl, $C_{1-8}$alkylheteroaryl, or $C_{1-8}$alkylheterocyclyl.

2. The compound according to claim 1, wherein $R_1$ is halogen.

3. The compound according to claim 2, wherein $R_1$ is fluoro.

4. The compound according to claim 1, wherein $R_2$ is halogen or hydrogen.

5. The compound according to claim 4, wherein $R_2$ is fluoro.

6. The compound according to claim 1, wherein $Q_2$ is phenyl or halo-substituted phenyl.

7. The compound according to claim 6, wherein $Q_2$ is 2-fluorophenyl or 4-fluorophenyl.

8. The compound according to claim 1, wherein $Q_3$ is phenyl or halo-substituted phenyl.

9. The compound according to claim 8, wherein $Q_3$ is halo-substituted phenyl.

10. The compound according to claim 9, wherein $Q_3$ is fluoro-substituted phenyl.

11. The compound according to claim 1, wherein $R_7$ is $C_{1-6}$alkyl, phenyl, or halo-substituted phenyl.

12. The compound according to claim 11, wherein $R_7$ is —$CH_3$ or fluoro-substituted phenyl.

13. The compound according to claim 1, wherein $R_7$, $R_8$ and $R_{11}$ are each independently hydrogen, halogen, or $C_{1-8}$alkyl.

14. The compound according to claim 13, wherein $R_7$, $R_8$ and $R_{11}$ are each hydrogen.

15. The compound according to claim 1, wherein

is a monocyclic 5, 6, 7, 8, 9, 10, 11, 12, 14, 16, or 18 membered heterocyclyl.

16. The compound according to claim 1, wherein

is a monocyclic 5, 7, 9, 11, 12, or 18 membered heterocyclyl.

17. The compound according to claim 1, wherein

contains 1, 2, 3, 4, 5, or 6 heteroatoms each independently selected from the group consisting of oxygen and nitrogen.

18. The compound according to claim 1, wherein

is

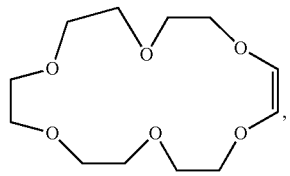

-continued

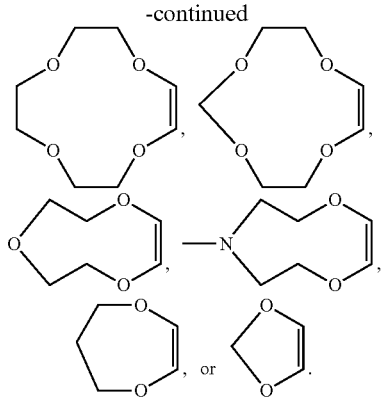

19. The compound according to claim 18, wherein

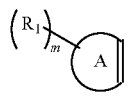

is

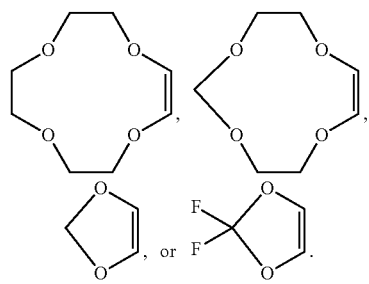

20. The compound according to claim 1, wherein m is 0, 1, or 2.

21. The compound according to claim 1, wherein $R_1$ is fluoro and m is 1 or 2.

22. The compound according to claim 1, wherein $A_2$ is =N—.

23. The compound according to claim 1, wherein $A_1$ is =C($R_2$)—, and $R_2$ is halogen, hydrogen, trihalomethyl, —CN, —$NO_2$, or —$NH_2$.

24. The compound according to claim 1, wherein $A_1$ is =CH— and $A_2$ is =N—.

25. The compound according to claim 1, wherein $A_1$ is =CH— or =CF—, and $A_2$ is =CH—.

26. The compound according to claim 1, wherein $A_3$ is =N— or =C(H)—.

27. The compound according to claim 1, wherein X is $NR_{20}$ or $CHR_{21}$, and $R_{20}$ and $R_{21}$ are each independently H or $C_{1-3}$alkyl.

28. The compound according to claim 1, wherein X is O, S, or NH.

29. The compound according to claim 1, wherein $R_3$ is $C_{1-4}$alkyl.

30. The compound according to claim 1, wherein $R_3$ is hydrogen.

31. The compound according to claim 1, wherein each $Q_1$ is $CH_2$.

32. The compound according to claim 1, wherein $R_4$ is

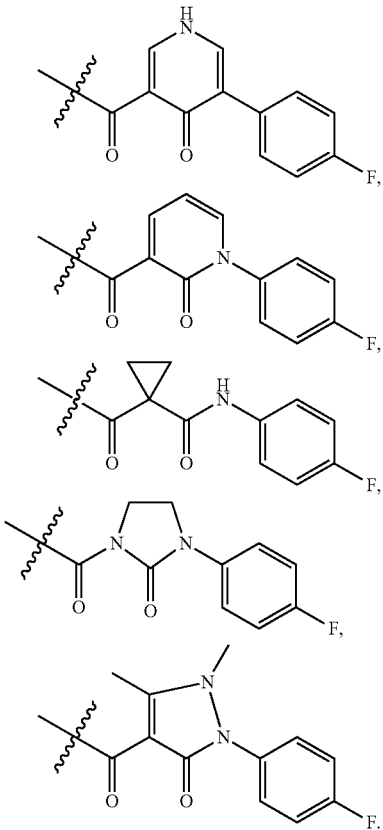

33. The compound according to claim 1, wherein $X_1$ is $NR_8$ and $R_8$ is $C_{1-6}$alkyl.

34. The compound according to claim 1, wherein $X_1$ is $NCH_3$.

35. The compound according to claim 1, wherein $R_8$ is hydrogen.

36. The compound according to claim 1, wherein $R_5$ and $R_6$ are each independently hydrogen.

37. The compound according to claim 1, wherein Z is

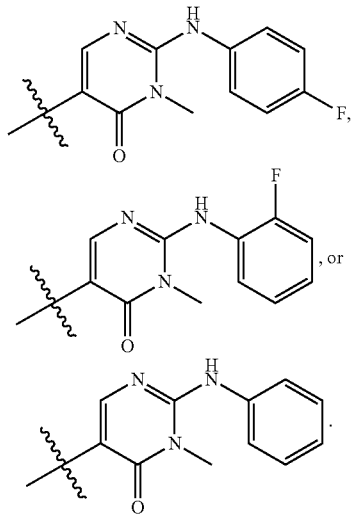

38. The compound according to claim 1, wherein the compound is selected from the group consisting of:

5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1,3-diaza-cyclododeca[b]naphthalen-4-yloxy)-phenyl]-amide;

1-(4-Fluoro-phenyl)-2-oxo-1,2-dihydro-pyridine-3-carboxylic acid [3-fluoro-4-(7,8,10,11,13,14-hexahydro-6,9,12,15-tetraoxa-1,3-diaza-cyclododeca[b]naphthalen-4-yloxy)-phenyl]-amide;

Cyclopropane-1,1-dicarboxylic acid [3-fluoro-4-(7,8,10,11,13,14-hexahydro-6,9,12,15-tetraoxa-1,3-diaza-cyclododeca[b]naphthalen-4-yloxy)-phenyl]-amide (4-fluoro-phenyl)-amide;

3-(4-Fluoro-phenyl)-2-oxo-imidazolidine-1-carboxylic acid [3-fluoro-4-(7,8,10,11,13,14-hexahydro-6,9,12,15-tetraoxa-1,3-diaza-cyclododeca[b]naphthalen-4-yloxy)-phenyl]-amide;

2-(4-Fluoro-phenyl)-1,5-dimethyl-3-oxo-2,3-dihydro-1H-pyrazole-4-carboxylic acid [3-fluoro-4-(7,8,10,11,13,14-hexahydro-6,9,12,15-tetraoxa-1,3-diaza-cyclododeca[b]naphthalen-4-yloxy)-phenyl]-amide;

2-(4-Fluoro-phenylamino)-5-[5-(7,8,10,11,13,14-hexahydro-6,9,12,15-tetraoxa-1,3-diaza-cyclododeca[b]naphthalen-4-yloxy)-pyridin-2-yl]-3-methyl-3H-pyrimidin-4-one;

5-[5-([1,3]Dioxolo[4,5-g]quinazolin-8-yloxy)-pyridin-2-yl]-2-(4-fluoro-phenylamino)-3-methyl-3H-pyrimidin-4-one;

5-[5-(2,2-Difluoro-[1,3]dioxolo[4,5-g]quinazolin-8-yloxy)-pyridin-2-yl]-2-(4-fluoro-phenylamino)-3-methyl-3H-pyrimidin-4-one;

5-(4-Fluoro-phenyl)-4-oxo-1,4-dihydro-pyridine-3-carboxylic acid [4-([1,3]dioxolo[4,5-g]quinazolin-8-yloxy)-3-fluoro-phenyl]-amide;

5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1-aza-cyclododeca[b]naphthalen-4-yloxy)-phenyl]-amide;

1-(4-Fluoro-phenyl)-2-oxo-1,2-dihydro-pyridine-3-carboxylic acid [3-fluoro-4-(7,8,10,11,13,14-hexahydro-6,9,12,15-tetraoxa-1-aza-cyclododeca[b]naphthalen-4-yloxy)-phenyl]-amide;

2-(4-Fluoro-phenyl)-1,5-dimethyl-3-oxo-2,3-dihydro-1H-pyrazole-4-carboxylic acid [3-fluoro-4-(7,8,10,11,13,14-hexahydro-6,9,12,15-tetraoxa-1-aza-cyclododeca[b]naphthalen-4-yloxy)-phenyl]-amide;

Cyclopropane-1,1-dicarboxylic acid [3-fluoro-4-(7,8,10,11,13,14-hexahydro-6,9,12,15-tetraoxa-1-aza-cyclododeca[b]naphthalen-4-yloxy)-phenyl]-amide (4-fluoro-phenyl)-amide;

3-(4-Fluoro-phenyl)-2-oxo-imidazolidine-1-carboxylic acid [3-fluoro-4-(7,8,10,11,13,14-hexahydro-6,9,12,15-tetraoxa-1-aza-cyclododeca[b]naphthalen-4-yloxy)-phenyl]amide;

5-[5-(2,2-Difluoro-[1,3]dioxolo[4,5-g]quinazolin-8-yloxy)-pyridin-2-yl]-2-(2-fluoro-phenylamino)-3-methyl-3H-pyrimidin-4-one;

5-[5-(2,2-Difluoro-[1,3]dioxolo[4,5-g]quinazolin-8-yloxy)-pyridin-2-yl]-2-(phenylamino)-3-methyl-3H-pyrimidin-4-one;

5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1-aza-cyclododeca[b]naphthalen-4-ylamino)-phenyl]-amide;

5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1-aza-cyclododeca[b]naphthalen-4-ylsulfanyl)-phenyl]-amide;

3-Methyl-2-phenylamino-5-[5-(2,5,7,10-tetraoxa-14,16-diaza-tricyclo[9.8.0.013,18]nonadeca-1(11),12,14,16,18-pentaen-17-yloxy)-pyridin-2-yl]-3H-pyrimidin-4-one;

5-[5-(8,9-Dihydro-7H-6,10-dioxa-1,3-diaza-cyclohepta[b]naphthalen-4-yloxy)-pyridin-2-yl]-2-(4-fluoro-phenylamino)-3-methyl-3H-pyrimidin-4-one;

2-(4-Fluoro-phenylamino)-3-methyl-5-[5-(9-methyl-8,9,10,11-tetrahydro-7H-6,12-dioxa-1,3,9-triaza-cyclonona[b]naphthalen-4-yloxy)-pyridin-2-yl]-3H-pyrimidin-4-one;

2-(4-Fluoro-phenylamino)-3-methyl-5-[5-(7,8,10,11-tetrahydro-6,9,12-trioxa-1,3-diaza-cyclonona[b]naphthalen-4-yloxy)-pyridin-2-yl]-3H-pyrimidin-4-one;

5-[5-(8,9-Dihydro-7H-6,10-dioxa-1-aza-cyclohepta[b]naphthalen-4-yloxy)-pyridin-2-yl]-2-(4-fluoro-phenylamino)-3-methyl-3H-pyrimidin-4-one;

2-(4-Fluoro-phenylamino)-3-methyl-5-[5-(9-methyl-8,9,10,11-tetrahydro-7H-6,12-dioxa-1,9-diaza-cyclonona[b]naphthalen-4-yloxy)-pyridin-2-yl]-3H-pyrimidin-4-one;

2-(4-Fluoro-phenylamino)-3-methyl-5-[5-(7,8,10,11-tetrahydro-6,9,12-trioxa-1-aza-cyclonona[b]naphthalen-4-yloxy)-pyridin-2-yl]-3H-pyrimidin-4-one;

3-Methyl-2-phenylamino-5-[5-(2,5,7,10-tetraoxa-14-aza-tricyclo[9.8.0.013,18]nonadeca-1(11),12,14,16,18-pentaen-17-yloxy)-pyridin-2-yl]-3H-pyrimidin-4-one;

5-[5-(2,2-Difluoro-[1,3]dioxolo[4,5-g]quinolin-8-yloxy)-pyridin-2-yl]-2-(2-fluoro-phenylamino)-3-methyl-3H-pyrimidin-4-one;

5-[5-(2,2-Difluoro-[1,3]dioxolo[4,5-g]quinolin-8-yloxy)-pyridin-2-yl]-2-(phenylamino)-3-methyl-3H-pyrimidin-4-one;

5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1,3-diaza-cyclododeca[b]naphthalen-4-ylamino)-phenyl]-amide;

5-(4-Fluoro-phenyl)-4-oxo-1,4-dihydro-pyridine-3-carboxylic acid [3-fluoro-4-(7,8,10,11,13,14-hexahydro-6,9,12,15-tetraoxa-1,3-diaza-cyclododeca[b]naphthalen-4-ylsulfanyl)-phenyl]-amide; and 5-[5-(2,5,8,11,14,17-Hexaoxa-21-aza-tricyclo[16.8.0.020,25]hexacosa-1(18),19,21,23,25-pentaen-24-yloxy)-pyridin-2-yl]-3-methyl-2-phenylamino-3H-pyrimidin-4-one.

39. A pharmaceutical composition comprising a compound according to claim 1 and at least one pharmaceutically acceptable excipient.

40. The pharmaceutical composition according to claim 39, wherein the weight ratio of the compound to the excipient ranges from 0.0001 to 10.

41. A method for inhibiting c-Met tyrosine kinase activity in a mammal, comprising administering to said mammal a therapeutically effective amount of at least one compound according to claim 1.

42. The method according to claim 41, wherein the mammal suffers from a disease or disorder selected from the group consisting of cancer, cancer metastasis, a cardiovascular disease, an immunological disorder, and an ocular disorder.

43. The method according to claim 42, wherein the cancer is selected from the group consisting of lung cancer, breast cancer, colorectal cancer, renal cancer, pancreatic cancer, head cancer, neck cancer, gastric cancer, hereditary papillary renal cell carcinoma, and childhood hepatocellular carcinoma.

\* \* \* \* \*